(12) United States Patent
Takagi et al.

(10) Patent No.: US 11,576,656 B2
(45) Date of Patent: Feb. 14, 2023

(54) ULTRASOUND IMAGE PROCESSING METHOD AND ULTRASOUND DIAGNOSTIC DEVICE USING SAME

(71) Applicant: KONICA MINOLTA, INC., Tokyo (JP)

(72) Inventors: Kazuya Takagi, Machida (JP); Yoshihiro Takeda, Hachioji (JP); Akihiro Kawabata, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 841 days.

(21) Appl. No.: 16/460,212

(22) Filed: Jul. 2, 2019

(65) Prior Publication Data

US 2019/0321006 A1    Oct. 24, 2019

Related U.S. Application Data

(62) Division of application No. 14/700,490, filed on Apr. 30, 2015, now Pat. No. 10,383,603.

(30) Foreign Application Priority Data

May 8, 2014    (JP) .................................. 2014-097182

(51) Int. Cl.
    *A61B 8/08*    (2006.01)
    *A61B 8/13*    (2006.01)
    (Continued)

(52) U.S. Cl.
    CPC .......... *A61B 8/5253* (2013.01); *A61B 8/0841* (2013.01); *A61B 8/13* (2013.01);
    (Continued)

(58) Field of Classification Search
    None
    See application file for complete search history.

(56) References Cited

U.S. PATENT DOCUMENTS

| 6,524,247 B2 | 2/2003 | Zhao et al. |
| 2005/0101865 A1 | 5/2005 | Hao et al. |

(Continued)

FOREIGN PATENT DOCUMENTS

| JP | 2000107178 A | 4/2000 |
| JP | 2001269339 A | 10/2001 |

(Continued)

OTHER PUBLICATIONS

Japanese Office Action dated Dec. 12, 2017 issued in counterpart Japanese Application No. 2014-097182.

*Primary Examiner* — Luther Behringer
(74) *Attorney, Agent, or Firm* — Holtz, Holtz & Volek PC

(57) ABSTRACT

An ultrasound diagnostic device generates a frame reception signal by compounding sub-frame reception signals acquired from a subject body through an ultrasound probe. The sub-frame reception signals are generated through sub-scans composing an ultrasound scan. Between the sub-scans, a range in the scanned subject body differs due to a different ultrasound beam steering angle used. The diagnostic device includes a control circuit with a reception signal acquirer acquiring sub-frame reception signals, and a map creator creating sub-frame enhancement maps corresponding to the sub-frame reception signals, the maps created by calculating, for a pixel region reception signal, an enhancement amount according to a characteristic value calculated based on the pixel region reception signal. The diagnostic device also includes an enhancement-applied reception signal generator generating an enhancement-applied frame reception signal by compounding pixel region reception signals considering the enhancement amount included in at least one sub-frame enhancement map.

4 Claims, 26 Drawing Sheets

(51) Int. Cl.
*A61B 8/00* (2006.01)
*G01S 15/89* (2006.01)

(52) U.S. Cl.
CPC ............ *A61B 8/5207* (2013.01); *A61B 8/461* (2013.01); *G01S 15/8995* (2013.01)

(56) References Cited

U.S. PATENT DOCUMENTS

| | | |
|---|---|---|
| 2006/0241451 A1* | 10/2006 | Nakaya .................. A61B 8/463 600/443 |
| 2009/0225827 A1 | 9/2009 | Sang et al. |
| 2012/0209107 A1 | 8/2012 | Guo et al. |
| 2013/0072785 A9 | 3/2013 | Guo et al. |
| 2013/0253325 A1 | 9/2013 | Call et al. |
| 2014/0187942 A1 | 7/2014 | Wang et al. |

FOREIGN PATENT DOCUMENTS

| | | |
|---|---|---|
| JP | 2012120747 A | 6/2012 |
| JP | 2012135617 A | 7/2012 |

* cited by examiner

FIG. 3

| Ultrasound scan | Sub-scan | B-mode image signal | | | | Enhancement map (motion amount) | | | | Enhancement-applied B-mode image signal |
|---|---|---|---|---|---|---|---|---|---|---|
| | | Sub-frame | Sub-frame | Sub-frame | Frame | Sub-frame | Sub-frame | Sub-frame | Frame (k) | Frame |
| 1 | 1 | 1 | | | | — | | | | |
| | 2 | | 2 | | | | — | | | |
| | 3 | | | 3 | 1+2+3 | | | — | — | 1+2+3 |
| 2 | 4 | 4 | | | | 4−1 | | | | |
| | 5 | | 5 | | | | 5−2 | | | |
| | 6 | | | 6 | 4+5+6 | | | 6−3 | 4+5+6 −1−2−3 | (4+5+6) x(k) |
| 3 | 7 | 7 | | | | 7−4 | | | | |
| | 8 | | 8 | | | | 8−5 | | | |
| | 9 | | | 9 | 7+8+9 | | | 9−6 | 7+8+9 −4−5−6 | (7+8+9) x(k) |
| 4 | 10 | 10 | | | | 10−7 | | | | |
| | 11 | | 11 | | | | 11−8 | | | |
| | 12 | | | 12 | 10+11+12 | | | 12−9 | 10+11+12 −7−8−9 | (10+11+12) x(k) |

B-mode image signal

B-mode image signal

Motion amount

Enhancement map

B-mode image signal

FIG. 18

| Ultrasound scan | Sub-scan | Acoustic line signal | | | | Enhancement map (edge enhancement) | | | | Enhancement-applied acoustic line signal | |
|---|---|---|---|---|---|---|---|---|---|---|---|
| | | Sub-frame | Sub-frame | Sub-frame | Frame | Sub-frame | Sub-frame | Sub-frame | Frame (k) | Frame |
| 1 | 1 | 1 | | | — | 1 | | | — | | — |
| | 2 | | 2 | | — | | | 2 | — | | — |
| | 3 | | | 3 | 1+2+3 | | 3 | | 1+2+3 | | (1+2+3) x(k) |
| 2 | 4 | 4 | | | 2+3+4 | 4 | | | 2+3+4 | | (2+3+4) x(k) |
| | 5 | | 5 | | 3+4+5 | | | 5 | 3+4+5 | | (3+4+5) x(k) |
| | 6 | | | 6 | 4+5+6 | | 6 | | 4+5+6 | | (4+5+6) x(k) |
| 3 | 7 | 7 | | | 5+6+7 | 7 | | | 5+6+7 | | (5+6+7) x(k) |
| | 8 | | 8 | | 6+7+8 | | | 8 | 6+7+8 | | (6+7+8) x(k) |
| | 9 | | | 9 | 7+8+9 | | 9 | | 7+8+9 | | (7+8+9) x(k) |
| 4 | 10 | 10 | | | 8+9+10 | 10 | | | 8+9+10 | | (8+9+10) x(k) |
| | 11 | | 11 | | 9+10+11 | | | 11 | 9+10+11 | | (9+10+11) x(k) |
| | 12 | | | 12 | 10+11+12 | | 12 | | 10+11+12 | | (10+11+12) x(k) |

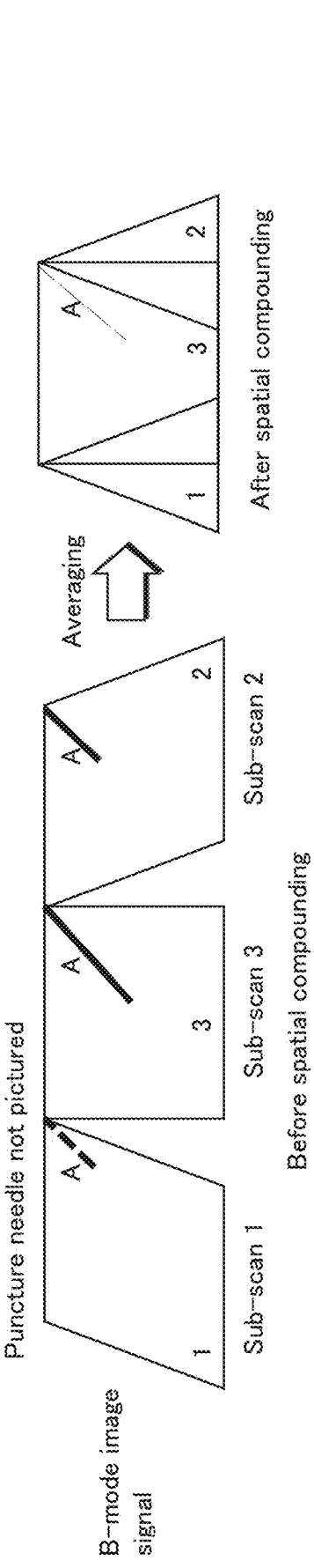
FIG.24A
FIG.24B
FIG.24C

Reception signal

Reception signal

Motion amount
(difference between frames)

Enhancement map

B-mode image signal

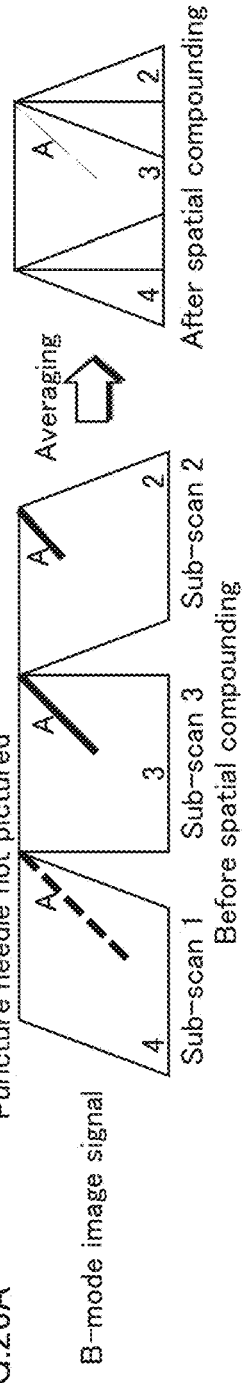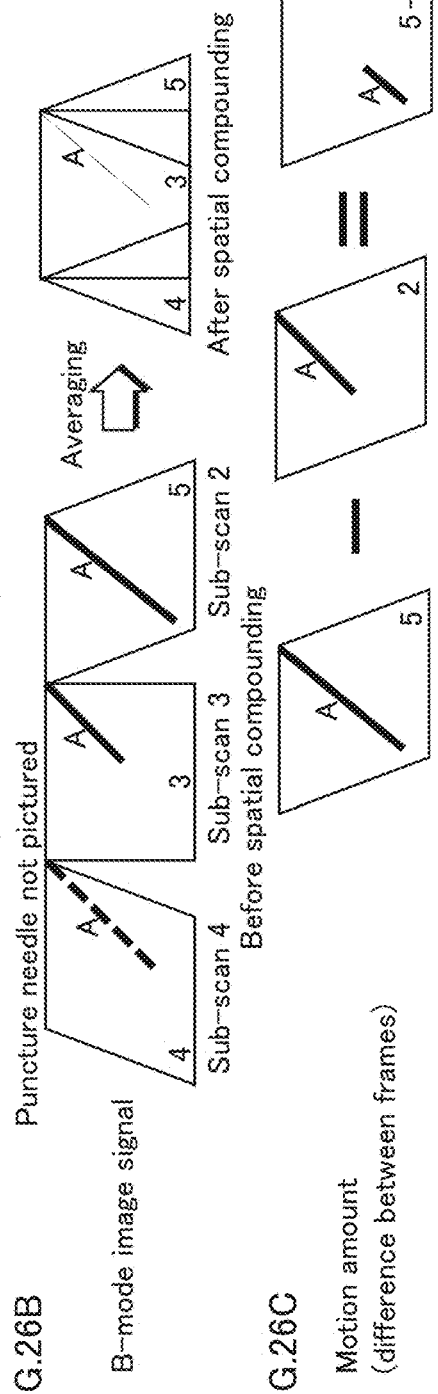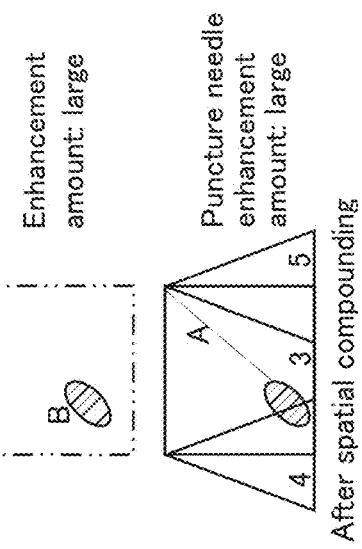

ULTRASOUND IMAGE PROCESSING METHOD AND ULTRASOUND DIAGNOSTIC DEVICE USING SAME

This application is a Divisional Application of U.S. Serial application Ser. No. 14/700,490, filed Apr. 30, 2015, (now issued as U.S. Pat. No. 10,383,603), which is based on Japanese Application No. 2014-097182, filed May 8, 2014, the contents of both of which are hereby incorporated by reference.

BACKGROUND OF DISCLOSURE

(1) Technical Field

The present disclosure pertains to an ultrasound image processing method and to an ultrasound diagnostic device using the ultrasound image processing method, and particularly pertains to ultrasound image diagnostic technology using spatial compounding.

(2) Description of the Related Art

In recent years, biological composition diagnostics are being performed by inserting a puncture needle into the body of a patient serving as the subject body, and taking samples of tissue, bodily fluids, or similar for diagnosis. Also, anesthesiologists, intensive care units, pain clinics, and the like use puncture needles for anesthetic treatment. Such diagnostics are realized by an operator, such as a doctor, performing the puncture with the puncture needle by using an ultrasound probe to acquire the position of the puncture needle within the body in an ultrasound image. This requires positional confirmation of the puncture needle, specifically a tip of the puncture needle, on a monitor. Thus, an ultrasound diagnostic device providing visibility improvements for the puncture needle is sought.

In response, in recent years, an ultrasound puncture system has been proposed, such as Japanese Patent Application Publication No. 2000-107178, in which a high-brightness portion is extracted from a cross-sectional ultrasound image based on a reception signal, and color is applied to the extracted portion for display as an overlay on the cross-sectional ultrasound image. Also, Japanese Patent Application Publication No. 2001-269339 proposes a method performed by an ultrasound diagnostic device of applying processing to cross-sectional ultrasound frame data that has been spatially modified by calculating a difference over time between pieces of cross-sectional ultrasound frame data. These documents describe obtaining a clear image of the puncture needle in the cross-sectional ultrasound image.

SUMMARY

Technical Problem

As it happens, the ultrasound diagnostic device applies a method of transmitting an ultrasound beam from an ultrasound probe into the subject body and making a reflected ultrasound (i.e., an echo signal) visible. Accordingly, for example, under conditions in which an angle of insertion of the puncture needle into the subject body is acute and the angle between the ultrasound beam and the puncture needle is thus small, the reflected ultrasound input to the ultrasound probe upon reflection by the puncture needle is weak, and the puncture needle is not made sufficiently visible. Thus, improvements are sought to the visibility of the puncture needle under such conditions.

Particularly, for reasons of obtaining a high signal-to-noise ratio and a wide field of view, in recent years, a widespread ultrasound image diagnostic has used a spatial compounding method of displaying a compound cross-sectional ultrasound image acquired from an ultrasound beam at a plurality of steering angles. However, the above-described phenomena are remarkable in such an ultrasound image diagnostic. That is, depending on the steering angle used for the ultrasound beam, the angle between the ultrasound beam and the puncture needle may be small. Further improvement to the visibility of the puncture needle is sought for such cases.

In consideration of the above-described problems, the present disclosure aims to provide an ultrasound image processing method, and an ultrasound diagnostic device using the method, enabling an improvement for the user to the visibility of the puncture needle during an ultrasound image diagnostic using spatial compounding.

Means for Solving the Problems

In order to resolve the above-described problem, an ultrasound image processing method pertaining to an aspect of the present disclosure is an ultrasound image processing method of generating a frame reception signal by compounding a plurality of sub-frame reception signals acquired from a subject body through an ultrasound probe, the sub-frame reception signals each being generated through one of a plurality of sub-scans composing an ultrasound scan, and between the sub-scans, a range in the subject body that is scanned differing due to a different one of a plurality of ultrasound beam steering angles being used, and involves acquiring the sub-frame reception signals, creating a plurality of sub-frame enhancement maps, each corresponding to one of the sub-frame reception signals, the creating of each of the sub-frame enhancement maps being performed by calculating, for a pixel region reception signal included in a corresponding one of the sub-frame reception signals, an enhancement amount in accordance with a characteristic value calculated based on the pixel region reception signal, the pixel region reception signal corresponding to a pixel region composed of one or more pixels, and generating an enhancement-applied frame reception signal by compounding pixel region reception signals included in the sub-frame reception signals based on pixel region positions, while taking into account the enhancement amount included in at least one of the sub-frame enhancement maps.

Also, an ultrasound diagnostic device pertaining to an aspect of the present disclosure generates a frame reception signal by compounding a plurality of sub-frame reception signals acquired from a subject body through an ultrasound probe, the sub-frame reception signals each being generated through one of a plurality of sub-scans composing an ultrasound scan, and between the sub-scans, a range in the subject body that is scanned differing due to a different one of a plurality of ultrasound beam steering angles being used, the ultrasound diagnostic device having a control circuit that includes a reception signal acquirer acquiring the sub-frame reception signals, a sub-frame enhancement map creator creating a plurality of sub-frame enhancement maps, each corresponding to one of the sub-frame reception signals, the creating of each of the sub-frame enhancement maps being performed by calculating, for a pixel region reception signal included in a corresponding one of the sub-frame reception signals, an enhancement amount in accordance with a characteristic value calculated based on the pixel region reception signal, the pixel region reception signal corresponding to a pixel region composed of one or more pixels, and an enhancement-applied reception signal generator generating an enhancement-applied frame reception signal by compounding pixel region reception signals included in the sub-frame reception signals based on pixel region positions, while taking into account the enhancement amount included in at least one of the sub-frame enhancement maps.

BRIEF DESCRIPTION OF THE DRAWINGS

These and the other objects, advantages, and features of the disclosure will become apparent from the following description thereof taken in conjunction with the accompanying drawings which illustrate a specific embodiment of the disclosure.

In the drawings:

FIG. 3 describes the operations of the ultrasound diagnostic device 10 pertaining to Embodiment 1;

FIG. 18 describes the operations of the ultrasound diagnostic device 10A pertaining to Embodiment 3;

FIGS. 24A, 24B, and 24C are schematic diagrams describing an example of a puncture needle enhancement operation performed by the ultrasound diagnostic device 10Y considered by the inventors;

FIGS. 26A through 26E are schematic diagrams describing another example of another puncture needle enhancement operation performed by the ultrasound diagnostic device 10Y considered by the inventors.

DESCRIPTION OF THE PREFERRED EMBODIMENTS

The following describes a preferred embodiment of the present disclosure.

<Background Leading to the Embodiment of the Disclosure>

The inventors considered various approaches to improving the visibility of a puncture needle during an ultrasound image diagnostic using spatial compounding.

Figure 19:
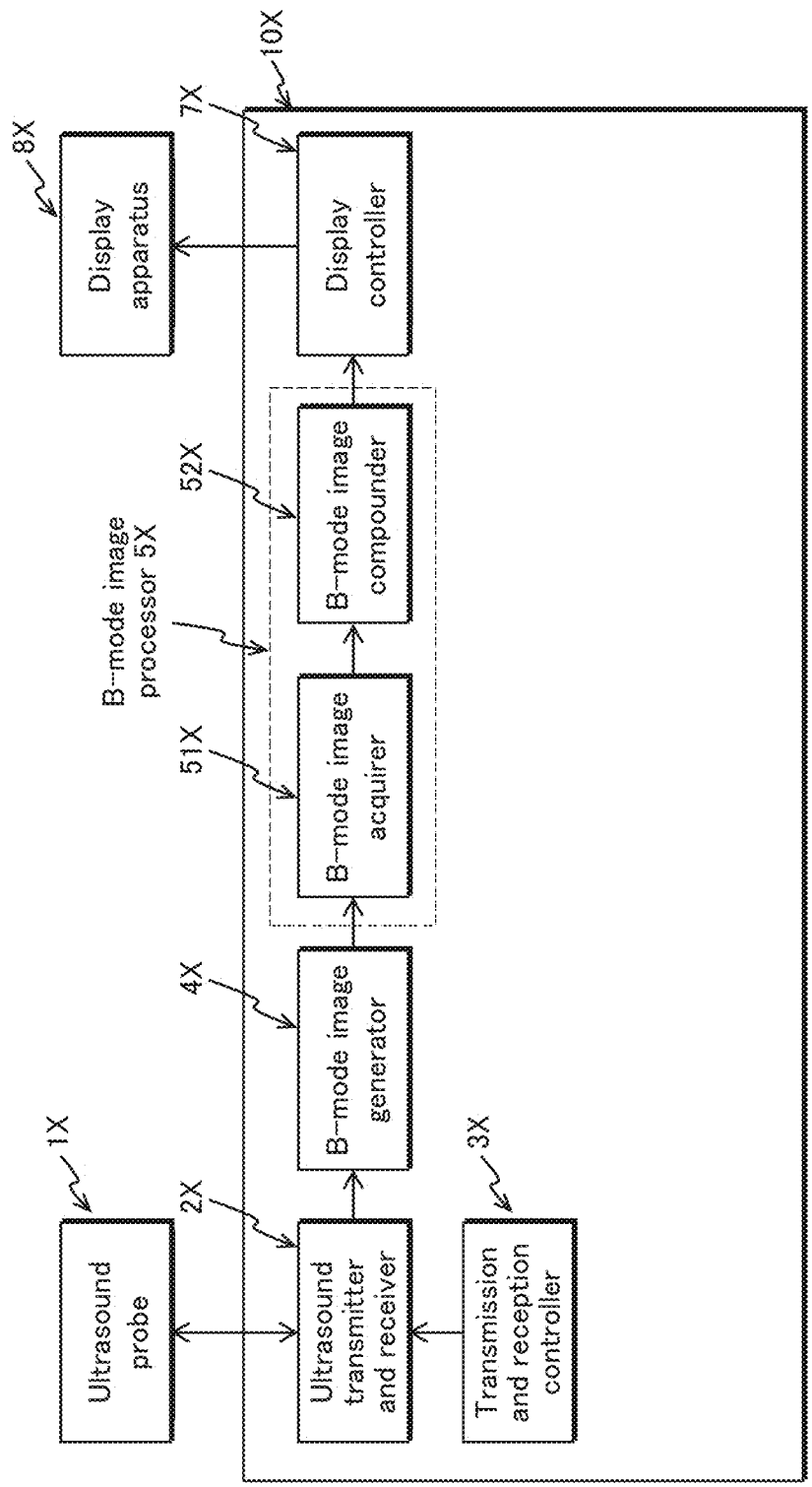
FIG. 19 is a functional block diagram of a conventional ultrasound diagnostic device 10X.

1. Puncture Needle Visibility in B-Mode Image using Spatial Compounding in Conventional Ultrasound Diagnostic Device 10X FIG. 19 is a block diagram indicating the configuration of a conventional ultrasound diagnostic device 10X. The ultrasound diagnostic device 10X includes an ultrasound transmitter and receiver 2X, a transmission and reception controller 3X, a B-mode image generator 4X, a B-mode image processor 5X, and a display controller 7X. The B-mode image processor 5X is made up of a B-mode image acquirer 51X and a B-mode image compounder 52X. Also, in the ultrasound diagnostic device 10X, an ultrasound probe 1X is connectable to the ultrasound transmitter and receiver 2X, and a display apparatus 8X is connectable to the display controller 7X.

Figure 20A:
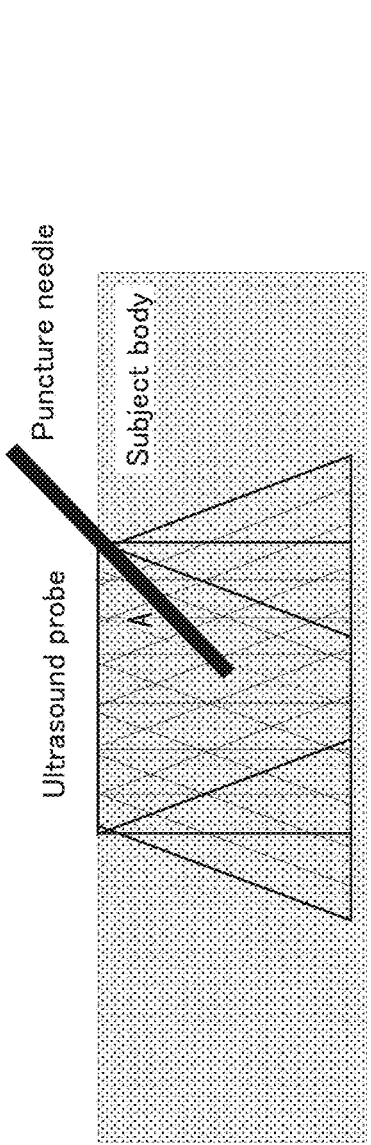
FIGS. 20A, 20B, and 20C are schematic diagrams describing operations of the conventional ultrasound diagnostic device 10X.
Figure 20B:
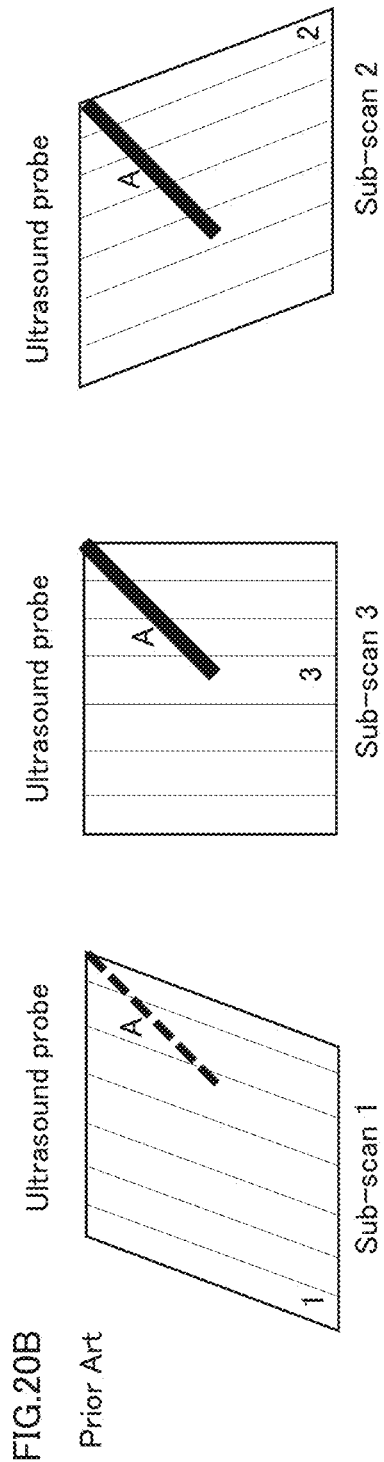
Figure 20C:
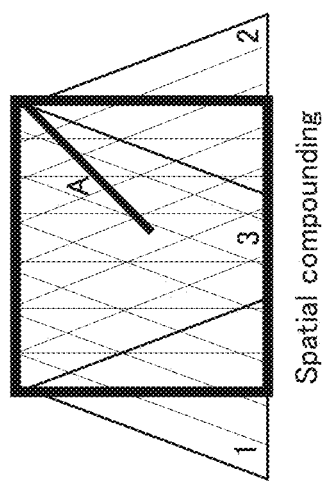

FIGS. 20A, 20B, and 20C are schematic diagrams describing operations of the conventional ultrasound diagnostic device 10X. As illustrated in FIG. 20A, the ultrasound diagnostic device 10X sequentially transmits and receives an ultrasound beam from a transducer array of the ultrasound probe 1X using, for example, a steering angle oriented in three directions across three stages. FIG. 20B is a schematic diagram individually depicting the transmission and reception of the ultrasound beam oriented in three directions (hereinafter termed sub-scan 1, sub-scan 2, and sub-scan 3 (the sub-scans in the three directions being collectively termed sub-scans when there is no need to distinguish between the three directions)).

According to FIG. 19, the ultrasound transmitter and receiver 2X performs a transmission process of supplying an ultrasound transmission signal in pulse form in accordance with a transmission control signal from the transmission and reception controller 3X, causing the ultrasound probe 1X to transmit the ultrasound beam. Here, the transmission control signal controlling the emission direction of the ultrasound beam in terms of the sub-scan is output from the transmission and reception controller 3X to the ultrasound transmitter and receiver 2X.

The ultrasound transmitter and receiver 2X also generates an acoustic line signal by amplifying an ultrasound signal based on a reflected ultrasound acquired from the ultrasound probe 1X and then performing delay-and-sum of an AD (analog-to-digital) converted RF (radio-frequency) signal that is continuous in the depth direction, and outputs the acoustic line signal to the B-mode image processor 5X. The acoustic line signal is then output to the B-mode image generator 4X in sub-scan order with respect to chronology.

The B-mode image generator 4X performs a brightness conversion by executing processing such as envelope detection, logarithmic compression, and so on with the acoustic line signal. A B-mode image signal is generated by applying conversion into Cartesian coordinates to a resulting brightness signal. The B-mode image signal generated by the B-mode image generator 4X is transmitted to and stored by the B-mode image acquirer 51X in chronological order for every sub-scan performed. The B-mode image acquirer 51X is a buffer storing the B-mode image signal.

The B-mode image compounder 52X acquires a B-mode sub-frame image signal acquired from the sub-scans performed by the B-mode image acquirer MX. As depicted in FIG. 20C, the B-mode image compounder 52X generates a B-mode frame image signal by compounding using a spatial compounding approach of averaging overlapping portions of the B-mode image signal acquired at the same location. The resulting B-mode image obtained by spatial compounding is displayed on the display apparatus 8X through the display controller 7X.

Figure 21:
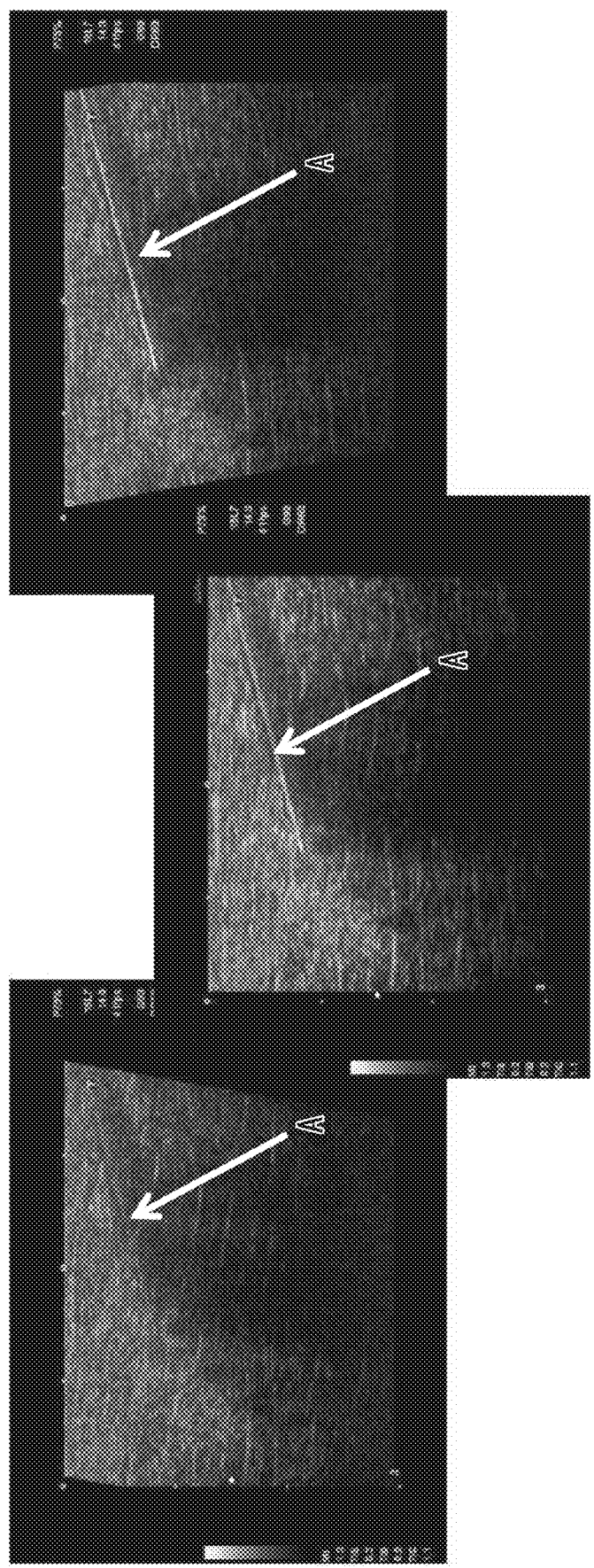
FIG. 21 depicts examples of a B-mode image resulting from displaying the B-mode sub-frame image signal acquired by the conventional ultrasound diagnostic device 10X.

FIG. 21 depicts examples of the B-mode image resulting from displaying the B-mode sub-frame image signal acquired by the conventional ultrasound diagnostic device 10X. The B-mode image signal includes sub-scans 1, 2, and 3 as depicted in FIG. 21, which correspond to the B-mode images from the B-mode sub-frame image signals obtained as schematically depicted for sub-scans 1, 2, and 3 in FIG. 20B. As indicated by the arrows in FIG. 21, the puncture needle (labeled A in FIG. 21) is inserted from the upper right to the lower right in terms of the image.

The ultrasound is reflected at a tissue boundary or the like, which is an acoustic interface between different matter. The reflection grows stronger as the angle with respect to the interface approaches 90 degrees, which produces a clear reflected ultrasound. Accordingly, when the angle between the puncture needle and the ultrasound beam is small, such as in sub-scan 1 of FIG. 21, the reflected ultrasound from the puncture needle is not received by the ultrasound probe 1X. As such, a strong and clear reflected ultrasound is not obtained. As a result, the puncture needle is barely distinguishable in the B-mode image from sub-scan 1.

In contrast, in sub-scan 2 and in sub-scan 3, the angle between the puncture needle and the ultrasound beam is larger, such that a strong and clear reflected ultrasound is obtained at the interface of the puncture needle. The reflected ultrasound is received by the ultrasound probe 1X and the puncture needle is clearly displayed in the B-mode image. According to experiments by the inventors, the visibility of the puncture needle is normally extremely low when the angle between the puncture needle and the ultrasound beam is 45 degrees or less.

Figure 22:
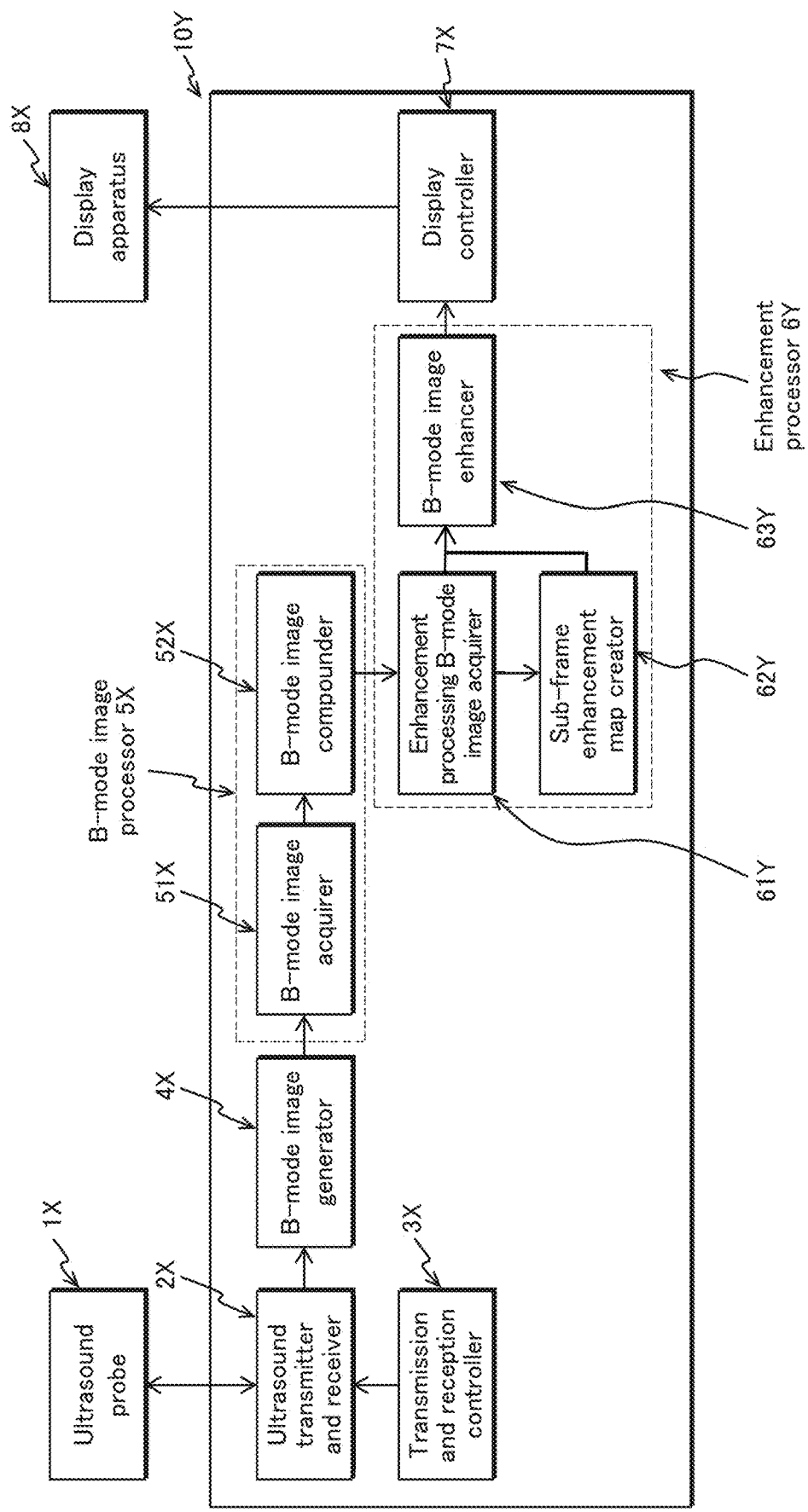
FIG. 22 is a functional block diagram of the ultrasound diagnostic device 10Y considered by the inventors.
Figure 23:
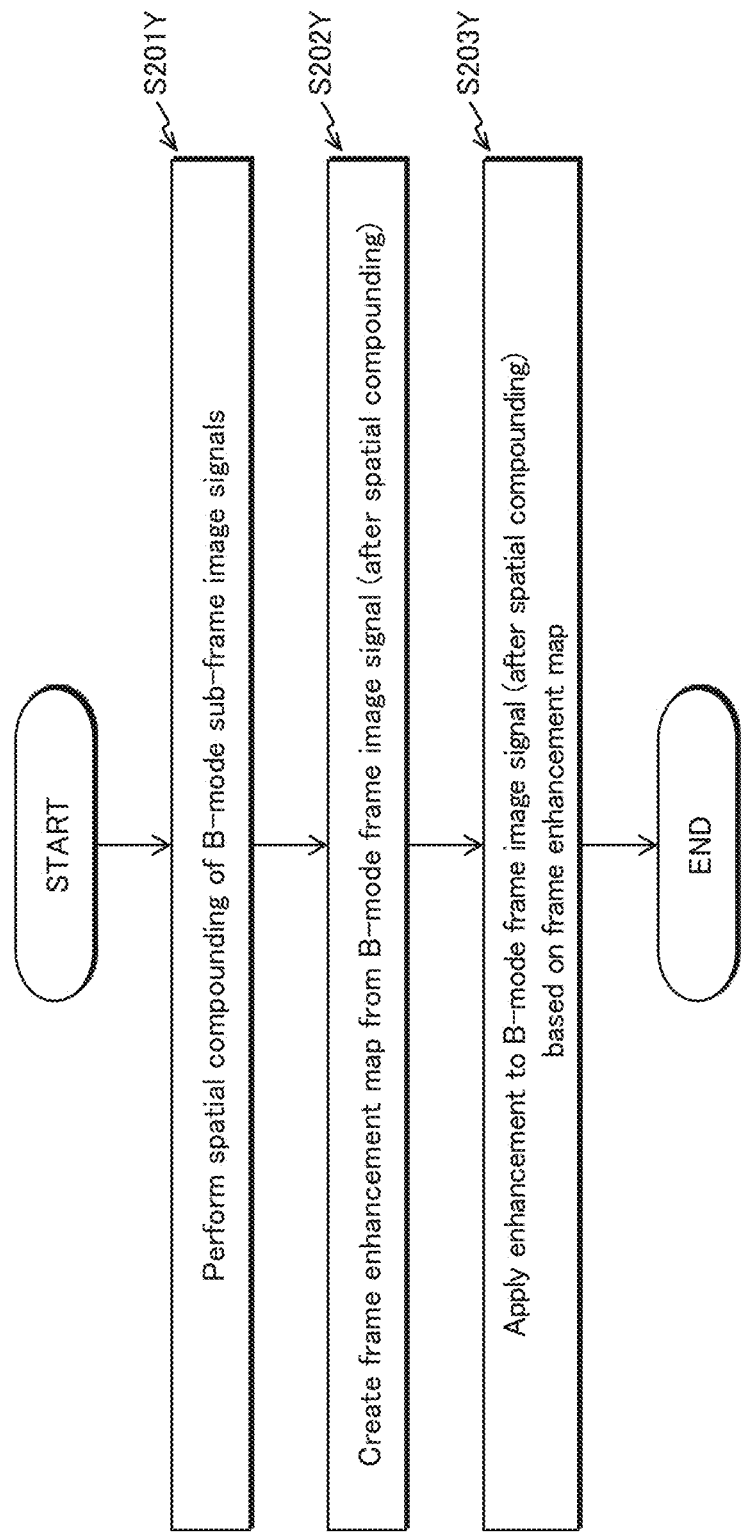
FIG. 23 is a flowchart of the operations performed by the ultrasound diagnostic device 10Y considered by the inventors.

Then, when the B-mode sub-frame image signal obtained from the sub-scans 1, 2, and 3 are used to generate the B-mode frame image signal by compounding using spatial compounding, the B-mode image signal indicating the puncture needle among the sub-frames is subject to averaging. As such, the visibility of the puncture needle is lower in the B-mode frame image than in sub-scan 2 and sub-scan 3, in which the puncture needle is clearly displayed. 2. Puncture Needle Visibility in B-Mode Image using Spatial Compounding in Ultrasound Diagnostic Device 10Y considered by Inventors (1) Edge Enhancement Processing The inventors considered improving the visibility of the puncture needle through edge enhancement processing applied to the B-mode image using spatial compounding. FIG. 22 is a functional block diagram of an ultrasound diagnostic device 10 Y considered by the inventors. The ultrasound diagnostic device 10Y differs from the ultrasound diagnostic device 10X in the addition of an enhancement processor 6Y to the configuration of the ultrasound diagnostic device 10X, and is otherwise identical in configuration to the ultrasound diagnostic device 10X. The enhancement processor 6Y includes an enhancement processing B-mode image acquirer 61Y, an sub-frame enhancement map creator 62Y, and a B-mode image enhancer 63Y. FIG. 23 is a flowchart indicating the operations of the B-mode image processor 5X and the enhancement processor 6Y in the ultrasound diagnostic device 10Y. FIGS. 24A, 24B, and 24C are schematic diagrams describing an example of a puncture needle enhancement operation performed by the ultrasound diagnostic device 10Y considered by the inventors.

In step S201Y of FIG. 23, the B-mode image compounder 52X reads the B-mode sub-frame image signal stored in the B-mode image acquirer 51X acting as a buffer. Then, as indicated in FIG. 24A, the B-mode image compounder 52X performs compounding by averaging overlapping portions of the B-mode image signal into a B-mode frame image signal, which is output to the enhancement processing B-mode image acquirer 61Y.

Next, in step S202Y, the sub-frame enhancement map creator 62Y reads the B-mode frame image signal from the enhancement processing B-mode image acquirer 61Y and, as illustrated in FIG. 24B, creates a frame enhancement map using edge enhancement processing, for example. The frame enhancement map is a signal array mapping an enhancement amount B to a portion extracted from the B-mode image signal, the puncture needle being present in the extracted portion. In the B-mode image signal, the brightness at the interface between the puncture needle and the subject body is dramatically different from the brightness of other regions of the subject body. Thus the puncture needle is extractable therefrom using edge enhancement or the like, for example.

Next, in step S203Y, the B-mode image enhancer 63Y reads the B-mode frame image signal from the enhancement processing B-mode image acquirer 61Y and, as depicted in FIG. 24C, applies enhancement processing to the B-mode frame image signal in accordance with the frame enhancement map created in step S202Y.

Here, when enhancement amount B has been appropriately mapped to the portion where the puncture needle is located in the frame enhancement map, then the enhancement processing is applied to portion A of the B-mode image signal where the puncture needle is located in the B-mode frame image signal. However, as described above, in the B-mode frame image signal (hereinafter termed B-mode frame image signal (1+2+3)) obtained by compounding the B-mode sub-frame image signals acquired in sub-scans 1, 2, and 3 (hereinafter termed B-mode sub-frame image signals 1, 2, and 3) the visibility of puncture needle A is lower in comparison to sub-scans 2 and 3, which are clear. Thus, the enhancement amount in the frame enhancement map created from the B-mode frame image signal (1+2+3) is also small. As a result, less enhancement is applied to the B-mode frame image signal upon enhancement processing.

(2) Motion Amount-Based Enhancement Processing

The inventors then considered improving the visibility of the puncture needle through motion amount-based enhancement processing applied to the B-mode image using spatial compounding. FIGS. 25A through 25E are schematic diagrams describing an example of a puncture needle enhancement operation performed by the ultrasound diagnostic device 10Y considered by the inventors. The flowchart of operations for the B-mode image processor 5Y and the enhancement processor 6Y is identical to FIG. 23.

Figure 25A:
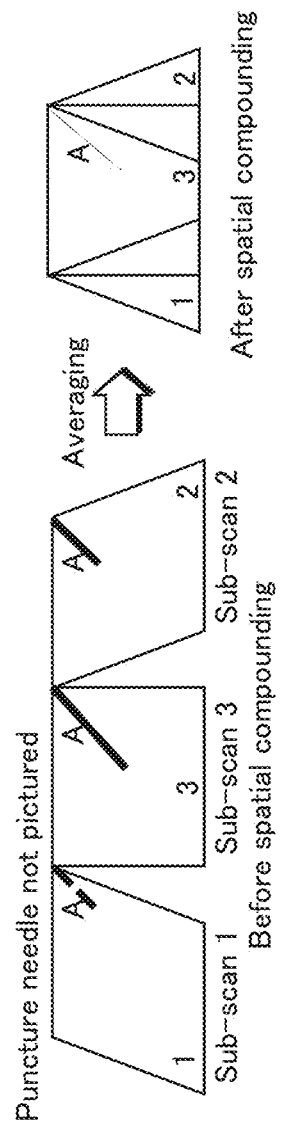
FIGS. 25A through 25E are schematic diagrams describing an example of another puncture needle enhancement operation performed by the ultrasound diagnostic device 10Y considered by the inventors.
Figure 25B:
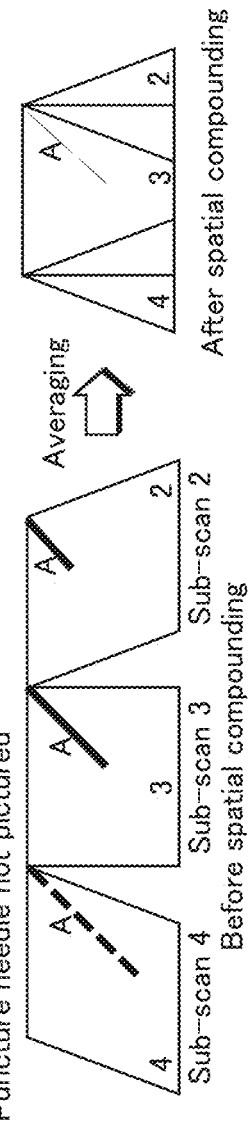

In step S201Y, the B-mode image compounder 52X reads the B-mode sub-frame image signals obtained through the sub-scans from the B-mode image acquirer 51X. Then, the B-mode image compounder 52X performs compounding by averaging overlapping portions of the B-mode image signal, thus generating a B-mode frame image signal, which is output to the enhancement processing B-mode image acquirer 61Y. The generation of the B-mode frame image signal is performed for each sub-scan. For example, as indicated in FIG. 25A, the B-mode frame image signal (1+2+3) is generated in accordance with the B-mode sub-frame image signals 1, 2, and 3 acquired during respective sub-scans 1, 2, and 3, the sub-scans 1, 2, and 3 having been performed in stages. Also, as indicated in FIG. 25B, sub-scan 4 is performed in an additional stage, and the B-mode frame image signal (2+3+4) is generated in accordance with the B-mode sub-frame image signals from three sub-frames acquired during respective sub-scans 2, 3 and 4. These B-mode frame image signals are sequentially output to the enhancement processing B-mode image acquirer 61Y and accumulated therein.

Figure 25C:
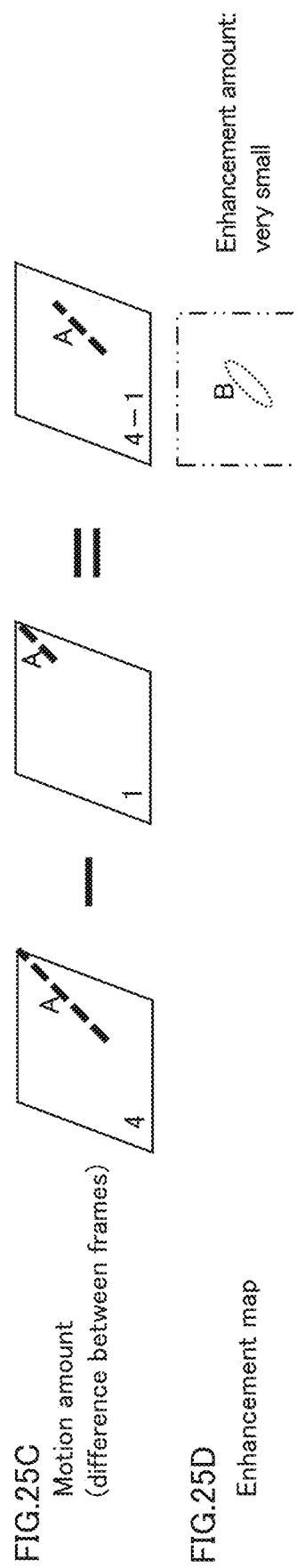
Figure 25D:
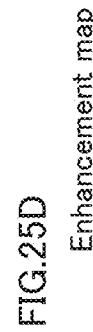

Next, in step S202Y, the sub-frame enhancement map creator 62Y reads two or more B-mode frame image signals including a current frame from the enhancement processing B-mode image acquirer 61Y, and computes a frame difference. The frame difference is the difference between the B-mode frame image signal of the current frame and the B-mode frame image signal of an earlier frame acquired at the same position on the subject body. When a pixel region includes a plurality of pixels, an average brightness of the pixels is usable to calculate the difference in brightness between pixel regions. Also, when three or more B-mode frame image signals are used to compute the frame difference, then for example, an average value or variance of a plurality of frame differences each calculated between two frames may be used. The frame enhancement map is created under conditions such that the greater the frame difference, the greater the enhancement amount with respect to the B-mode image signal. Using the above-described frame difference enables a portion of the B-mode image signal that indicates the displacement of the puncture needle to be extracted. As indicated in FIG. 25D, the frame enhancement map (4-1) is created based on the results of this frame difference and output to the enhancement processing B-mode image acquirer 61Y.

Figure 25E:

Next, in step S203Y, and as depicted in FIG. 25E, the B-mode image enhancer 63Y reads B-mode frame image signal (2+3+4) from the enhancement processing B-mode image acquirer 61Y, applies enhancement processing in accordance with the frame enhancement map (4-1) created in step S202Y, and thus generates B-mode frame image signal (2+3+4).

Here, when the enhancement amount has been appropriately mapped to the portion where the puncture needle is located in the frame enhancement map, then the enhancement processing is applied to the B-mode image signal at the portion where the puncture needle is mainly located in the B-mode frame image signal. However, as indicated in FIG. 25C, the frame difference between the B-mode frame image signal (1+2+3) obtained from sub-scans 1, 2, and 3 and the B-mode frame image signal (2+3+4) obtained from sub-scans 2, 3, and 4 is substantially equal to the frame difference between B-mode sub-frame image signal 4 (hereinafter termed B-mode sub-frame image signal 4) obtained from sub-scan 4 and B-mode sub-frame image signal 1 obtained from sub-scan 1, as depicted in FIG. 25C. B-mode sub-frame image signals 4 and 1 are obtained under conditions in which the angle between the puncture needle and the ultrasound beam is small, such that the puncture needle is not clearly depicted, and the puncture needle is thus barely noticeable. As such, the puncture needle remains difficult to detect despite calculating the motion amount between B-mode sub-frame image signals 4 and 1, and very little enhancement is produced in the frame enhancement map created according to the frame difference therebetween. As a result, and as indicated in FIG. 25E, very little enhancement is produced in B-mode frame image signal (2+3+4) after the enhancement processing.

FIGS. 26A through 26E are schematic diagrams describing an example of a puncture needle enhancement operation performed by the ultrasound diagnostic device 10Y. Here, sub-scan 5 has been added to the conditions depicted in FIG. 25B.

As indicated in FIG. 26A, B-mode frame image signal (2+3+4) is generated in accordance with the B-mode sub-frame image signals 2, 3 and 4 acquired during respective sub-scans 2, 3, and 4, with the sub-scans 2, 3, and 4 having been performed. Also, as indicated in FIG. 26B, sub-scan 5 is additionally performed, and B-mode frame image signal (3+4+5) is generated in accordance with the B-mode sub-frame image signals 3, 4, and 5 from three sub-frames acquired during respective sub-scans 3, 4, and 5.

Next, the frame difference between B-mode frame image signal (3+4+5) and B-mode frame image signal (2+3+4) is computed, producing frame enhancement map (5-2) as indicated in FIG. 26D.

Here, as indicated in FIG. 26C, the frame difference is substantially equal to the frame difference between B-mode sub-frame image signal 5 and B-mode sub-frame image signal 2. B-mode sub-frame image signals 5 and 2 are obtained under conditions in which the angle between the puncture needle and the ultrasound beam is large, such that the puncture needle is clearly indicated. Thus, the puncture needle is detectable in accordance with the motion amount detected from the frame difference. As indicated in FIG. 25D, a great enhancement amount is produced in frame enhancement map (5-2). As a result, and as indicated in FIG. 25E, a great enhancement amount is produced in B-mode frame image signal (3+4+5) after the enhancement processing.

Accordingly, when enhancing the puncture needle in the B-mode image obtained through spatial compounding by using a frame enhancement map created from the frame difference between B-mode frame image signals, there are cases where the enhancement amount for the puncture needle is extremely low in each cycle of sub-scan steering angle change.

As such, the inventors arrived at an ultrasound image processing method in which detection is performed using a frame enhancement map creation method that involves appropriately mapping enhancement to the puncture needle in puncture needle enhancement processing performed on a B-mode image using spatial compounding, and an ultrasound diagnostic device using the ultrasound image processing method pertaining to the Embodiments of the disclosure.

The ultrasound image processing method pertaining to the Embodiment and an ultrasound diagnostic device using the ultrasound image processing method are described below, with reference to the accompanying drawings.

<Overview of Aspects of the Disclosure>

An ultrasound image processing method pertaining to one aspect involves generating a frame reception signal by compounding a plurality of sub-frame reception signals acquired from a subject body through an ultrasound probe, the sub-frame reception signals each being generated through one of a plurality of sub-scans composing an ultrasound scan, and between the sub-scans, a range in the subject body that is scanned differing due to a different one of a plurality of ultrasound beam steering angles being used, the ultrasound image processing method involving acquiring the sub-frame reception signals, creating a plurality of sub-frame enhancement maps, each corresponding to one of the sub-frame reception signals, the creating of each of the sub-frame enhancement maps being performed by calculating, for a pixel region reception signal included in a corresponding one of the sub-frame reception signals, an enhancement amount in accordance with a characteristic value calculated based on the pixel region reception signal, the pixel region reception signal corresponding to a pixel region composed of one or more pixels, and generating an enhancement-applied frame reception signal by compounding pixel region reception signals included in the sub-frame reception signals based on pixel region positions, while taking into account the enhancement amount included in at least one of the sub-frame enhancement maps.

In another aspect, the generating of the enhancement-applied frame reception signal involves creating a frame enhancement map by averaging the sub-frame enhancement maps, generating a frame reception signal by compounding the sub-frame reception signals, and applying enhancement to the frame reception signal by applying, with respect to each pixel region reception signal included in the frame reception signal, an enhancement amount, included in the frame enhancement map, for a corresponding pixel region reception signal.

In a further aspect, the creating of the frame enhancement map comprises amplifying the frame enhancement map so that an enhancement amount included in the frame enhancement map that is equal to or greater than a predetermined value is amplified to reach or approach an upper limit.

In an additional aspect, the predetermined value is determined in accordance with a quantity of sub-frames to be compounded, the predetermined value increasing as the quantity of the sub-frames increases.

In yet another aspect, the generating of the enhancement-applied frame reception signal involves creating a frame enhancement map by compounding the sub-frame enhancement maps, in accordance with a correction condition pertaining to the ultrasound beam steering angles respectively used to acquire the sub-frame reception signals, generating a frame reception signal by compounding the sub-frame reception signals, and applying enhancement to the frame reception signal by applying, with respect to each pixel region reception signal included in the frame reception signal, an enhancement amount, included in the frame enhancement map, for a corresponding pixel region reception signal.

In still another aspect, the correction condition is using, as the frame enhancement map, a sub-frame enhancement map including a greatest enhancement amount, among the sub-frame enhancement maps.

In still a further aspect, the correction condition is using, as the frame enhancement map, a sub-frame enhancement maps based on a sub-scan corresponding to a steering angle around a center, among the sub-frame enhancement maps.

In still an additional aspect, the correction condition is creating the frame enhancement map by providing greater weight to a sub-frame enhancement map based on a sub-scan corresponding to a steering angle around a center, among the sub-frame enhancement maps, than a sub-frame enhancement map based on a sub-scan corresponding to a steering angles not around the center, among the sub-frame enhancement maps, and by compounding the sub-frame enhancement maps, to which weights have been provided.

In a further additional aspect, the correction condition is compounding a sub-frame enhancement map based on a sub-scan corresponding to a steering angle around a center, among the sub-frame enhancement maps, and a sub-frame enhancement map that is based on a sub-scan corresponding to a steering angle not around the center and that has a relatively great total enhancement amount, among the sub-frame enhancement maps, the total enhancement amount being a total of enhancement amounts in a sub-frame enhancement map.

In still a further aspect, the correction condition is using, as the frame enhancement map, a sub-frame enhancement map that is based on a sub-scan corresponding to a steering angle not around a center and that has a relatively great total enhancement amount, among the sub-frame enhancement maps, the total enhancement amount being a total of enhancement amounts in a sub-frame enhancement map.

In yet a further aspect, the correction condition is compounding a sub-frame enhancement map based on a sub-scan corresponding to a steering angle around a center, among the sub-frame enhancement maps, and a sub-frame enhancement map based on a sub-scan corresponding to a predetermined steering angle that is not around the center, among the sub-frame enhancement maps.

In yet another aspect, the correction condition is using, as the frame enhancement map, a sub-frame enhancement map based on a sub-scan corresponding to a predetermined steering angle that is not around the center, among the sub-frame enhancement maps.

In still yet another aspect, the generating of the enhancement-applied frame reception signal involves generating enhancement-applied sub-frame reception signals by applying, with respect to each pixel region reception signal included in each of the sub-frame reception signals, an enhancement amount, included in the corresponding sub-frame enhancement map, for a corresponding pixel region reception signal, and generating the enhancement-applied frame reception signal by averaging the enhancement-applied sub-frame reception signals.

In still a further aspect, the generating of the enhancement-applied frame reception signal involves generating enhancement-applied sub-frame reception signals by applying, with respect to each pixel region reception signal included in each of the sub-frame reception signals, an enhancement amount, included in the corresponding sub-frame enhancement map, for a corresponding pixel region reception signal, and compounding the enhancement-applied sub-frame enhancement maps, in accordance with a correction condition pertaining to the ultrasound beam steering angles respectively used to acquire the sub-frame reception signals.

In still yet a further aspect, the characteristic value calculated based on the pixel region reception signal is a difference between the pixel region reception signal and a pixel region reception signal for a same pixel region acquired in an earlier sub-scan at an identical steering angle as the given pixel region reception signal, the enhancement amount increasing as the difference increases.

In a yet a further additional aspect, the characteristic value based on the pixel region reception signal is a difference between the pixel region reception signal and a pixel region reception signal for a pixel region near the pixel region, the enhancement amount increasing as the difference increases.

In another additional aspect, a puncture needle is inserted into the subject body within the range in the subject body that is scanned, and in the frame enhancement map, an enhancement amount is mapped to a pixel region reception signal that, in the frame reception signal, indicates the puncture needle.

In yet a further additional aspect, the applying of the enhancement to the frame reception signal includes increasing brightness indicated by a pixel region reception signal, in the frame reception signal, to which an enhancement amount is mapped in the frame enhancement map.

In still yet a further additional aspect, the applying of the enhancement to the frame reception signal includes changing a color indicated by a pixel region reception signal, in the frame reception signal, to which an enhancement amount is mapped in the frame enhancement map.

In an alternative aspect, each reception signal is either an acoustic line signal generated in accordance with reflected ultrasound acquired by the ultrasound probe from the subject body, or a B-mode image signal obtained by conversion of the acoustic line signal into Cartesian coordinates.

In another alternative aspect, each reception signal is one of a B-mode image signal and an acoustic line signal.

In a further alternative aspect, a non-transitory computer-readable recording medium has recorded thereon a program causing a computer to execute the ultrasound image processing method.

In yet another alternative aspect, an ultrasound diagnostic device generates a frame reception signal a plurality of sub-frame reception signals acquired from a subject body through an ultrasound probe, the sub-frame reception signals each being generated through one of a plurality of sub-scans composing an ultrasound scan, and between the sub-scans, a range in the subject body that is scanned differing due to a different one of a plurality of ultrasound beam steering angles being used, the ultrasound diagnostic device having a control circuit that includes a reception signal acquirer acquiring the sub-frame reception signals, a sub-frame enhancement map creator creating a plurality of sub-frame enhancement maps, each corresponding to one of the sub-frame reception signals, the creating of each of the sub-frame enhancement maps being performed by calculating, for a pixel region reception signal included in a corresponding one of the sub-frame reception signals, an enhancement amount in accordance with a characteristic value calculated based on the pixel region reception signal, the pixel region reception signal corresponding to a pixel region composed of one or more pixels, and an enhancement-applied reception signal generator generating an enhancement-applied frame reception signal by compounding pixel region reception signals included in the sub-frame reception signals based on pixel region positions, while taking into account the enhancement amount included in at least one of the sub-frame enhancement maps.

In yet a further alternative aspect, the enhancement-applied reception signal generator includes a frame enhancement map compounder creating a frame enhancement map by averaging the sub-frame enhancement maps of the sub-frame reception signals, a reception signal generator generating a frame reception signal by compounding the sub-frame reception signals, and a reception signal enhancer applying enhancement to the frame reception signal by applying, with respect to each pixel region reception signal included in the frame reception signal, an enhancement amount, included in the frame enhancement map, for a corresponding pixel region reception signal.

In still yet a further alternative aspect, the enhancement-applied reception signal generator includes a frame enhancement map compounder creating a frame enhancement map by compounding the sub-frame enhancement maps, in accordance with a correction condition pertaining to the ultrasound beam steering angles respectively used to acquire the sub-frame reception signals, a reception signal compounder generating a frame reception signal by compounding the sub-frame reception signals, and a reception signal enhancer applying enhancement to the frame reception signal by applying, with respect to each pixel region reception signal included in the frame reception signal, an enhancement amount, included in the frame enhancement map, for a corresponding pixel region reception signal.

<Embodiment 1>

An ultrasound diagnostic device pertaining to Embodiment 1 is described below, with reference to the accompanying drawings.

<Overall Configuration>

1. Ultrasound Diagnostic Device

Figure 1:
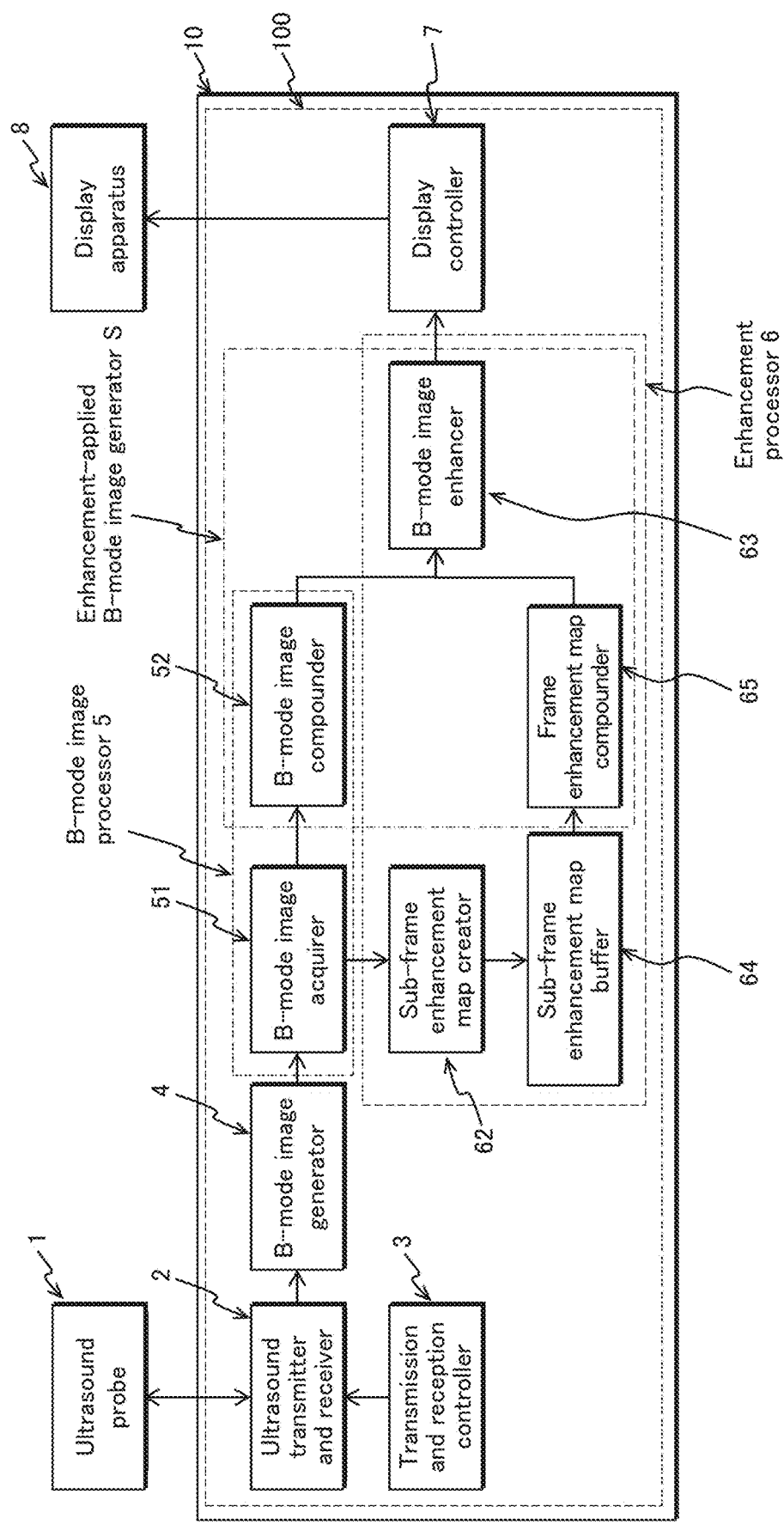
FIG. 1 is a functional block diagram of an ultrasound diagnostic device 10 pertaining to Embodiment 1.

FIG. 1 is a functional block diagram of an ultrasound diagnostic device 10 pertaining to Embodiment 1. The ultrasound diagnostic device 10 is configured from a control circuit 100 that includes an ultrasound transmitter and receiver 2, a transmission and reception controller 3, a B-mode image generator 4, a B-mode image processor 5, an enhancement processor 6, and a display controller 7. The components of the control circuit 100 are each realized as a hardware circuit such as, for example, a field programmable gate array (hereinafter, FPGA), an application specific integrated circuit (hereinafter, ASIC), or the like. Alternatively, the components may be realized by a central processing unit (hereinafter, CPU), a general-purpose computing on graphics processing unit (GPGPU), or similar in combination with a programmable device, such as a processor, and software. All of these components may be realized as a single circuit unit, or may be realized as a plurality of circuit units. Also, a plurality of components may be combined into a single circuit unit, or may be combined into a plurality of circuit units. Also, in the ultrasound diagnostic device 10, an ultrasound probe 1 is connectable to the ultrasound transmitter and receiver 2 and a display apparatus 8 is connectable to the display controller 7. The ultrasound diagnostic device 10 is depicted in FIG. 1 with the ultrasound probe 1 and the display apparatus 8 being connected.

Similarly to the conventional ultrasound diagnostic device 10X depicted in FIG. 20A, the ultrasound diagnostic device 10 sequentially transmits and receives an ultrasound beam from a transducer array of the ultrasound probe 1 using, for example, a steering angle oriented in three directions across three stages, the transmitting and receiving being performed in accordance with spatial compounding. In addition, and similarly to the example depicted in FIG. 20B, the transmission and reception of the ultrasound beam oriented in three directions includes sub-scan 1, sub-scan 2, and sub-scan 3 (the sub-scans in the three directions being collectively termed sub-scans when there is no need to distinguish between the three directions). A single ultrasound scan includes sub-scans 1, 2, and 3.

The components connected to the ultrasound diagnostic device 10 are described next.

2. Ultrasound Probe 1

The ultrasound probe 1 includes, for example, a plurality of transducers (undepicted) arranged in a mono-directional array (hereinafter termed the transducer array direction). The ultrasound probe 1 converts an electronic signal (hereinafter termed an ultrasound transmission signal) supplied in pulse form from the later-described ultrasound transmitter and receiver 2 into a pulse-form ultrasound.

The ultrasound probe 1 is arranged such that an outer transducer surface of the ultrasound probe 1 is placed in contact with a skin surface of a subject body, and transmits the ultrasound beam, made up of a plurality of ultrasounds emitted by the plurality of transducers, toward a measuring target. The ultrasound probe 1 then receives a plurality of reflected ultrasound waves from the subject body. The transducers convert each of these reflected ultrasounds into an electronic signal (hereinafter termed an ultrasound signal). The ultrasound probe 1 supplies the ultrasound signals to the ultrasound transmitter and receiver 2.

Also, in Embodiment 1, the ultrasound probe 1 is described as including a plurality of transducers arranged into a mono-directional array. However, no such limitation is intended to the ultrasound probe 1 usable by the present Embodiment. For instance, a two-dimensional transducer array in which the transducers are arranged in two dimensions may apply, as well as an oscillatory ultrasound probe acquiring cross-sectional images in three dimensions by dynamic oscillation of a plurality of transducers arranged in a mono-dimensional array. Adjustments may be applied in accordance with the measurement performed.

The ultrasound probe 1 may also be provided such that a portion of the functions of the later-described ultrasound transmitter and receiver 2 are performed by the ultrasound probe. For example, an electronic transmission signal may be generated within the ultrasound probe 1 in accordance with a control signal for generating the electronic transmission signal (hereinafter termed a transmission control signal) output from the ultrasound transmitter and receiver 2, and the ultrasound probe may be provided with functionality for converting the electronic transmission signal into ultrasound. Also, the ultrasound probe may be provided with functionality for converting the reflected ultrasound, upon receipt, into an electronic reception signal, and generating a later-described reception signal in accordance with the electronic reception signal.

3. Display Apparatus 8

The display apparatus 8 is a display device for image display, displaying an image output by the later-described display controller 7 on a display screen. The display apparatus 8 may use a liquid-crystal display, a cathode ray tube (hereinafter, CRT), an organic electroluminescence display, and so on.

<Component Configurations>

The configurations of the blocks in the ultrasound diagnostic device 10 are described next.

1. Ultrasound Transmitter and Receiver 2

The ultrasound transmitter and receiver 2 is connected to the ultrasound probe 1. The ultrasound transmitter and receiver 2 is a circuit performing a transmission process of supplying an ultrasound transmission signal in pulse form in accordance with a transmission control signal from the transmission and reception controller 3, for causing the ultrasound probe 1 to transmit the ultrasound beam. Specifically, the ultrasound transmitter and receiver 2 is equipped with, for example, a clock generation circuit, a pulse generation circuit, and a delay circuit. The clock generation circuit is a circuit producing a clock signal that determines the transmission timing of the ultrasound beam. The pulse generation circuit is a circuit for producing a pulse signal driving the transducers. The delay circuit is a circuit for setting a delay time for the ultrasound beam transmission timing of each of the transducers, and for focusing and steering the ultrasound beam by delaying transmission by the delay interval.

In the present Embodiment, the ultrasound transmitter and receiver 2 generates a transmission delay profile signal controlling the steering angle that determines the emission direction of the ultrasound beam for the sub-scan, in accordance with the transmission control signal produced by the transmission and reception controller 3 and indicating the direction of the sub-scan. The transmission delay profile signal is transmission delay profile information indicating the timing at which the transducers in the transducer array corresponding to the ultrasound beam formed by the ultrasound transmission signal are to be driven. The transducers in the transducer array are driven at the timing indicated by the transmission delay profile signal, determined in accordance with the steering angle for the sub-scan. Thus, the ultrasound beam is emitted at the appropriate steering angle.

The ultrasound transmitter and receiver 2 also generates an acoustic line signal that is continuous in the depth direction, by amplifying ultrasound signals based on reflected ultrasound waves acquired from the ultrasound probe 1 and then performing delay-and-sum of AD (analog to digital) converted RF (radio frequency) signals. A reception process is performed by outputting acoustic line signals for each sub-scan to the B-mode image generator 4 in sub-scan order with respect to chronology.

The RF signals are, for example, made up of a plurality of RF signals in the transducer array direction, each being a signal in a direction orthogonal to the transducer array direction, which is the direction of ultrasound transmission. Each RF signal is obtained by performing A/D conversion on an electronic signal obtained by converting the amplitude of a reflected ultrasounds wave.

The acoustic line signal is data continuous in the depth direction, made up of the RF signals after the delay-and-sum process. The depth direction is the direction in which the ultrasound transmission signal advances into the body from the surface of the subject body. A plurality of the acoustic line signals in the transducer array direction, each being a signal in the direction orthogonal to the transducer array direction, or that is, the transmission direction of the ultrasound, constructs a frame. The acoustic line signals acquired in each single sub-scan is termed sub-frame acoustic line signals.

The ultrasound transmitter and receiver 2 repeatedly and continuously performs the transmission process and the reception process.

2. Transmission and Reception Controller 3

The transmission and reception controller 3 is a circuit generating a transmission control signal and a reception control signal, and outputting these signals to the ultrasound transmitter and receiver 2. In the present Embodiment, the transmission control signal and the reception control signal are output to the ultrasound transmitter and receiver 2 along with information indicating the steering angle for the ultrasound beam in each sub-scan, in addition to the timing of transmission and reception and so on.

3. B-Mode Image Generator 4

The B-mode image generator 4 is a circuit generating a B-mode sub-frame image signal by converting each acoustic line signal within a sub-frame into a brightness signal corresponding to the intensity of the acoustic line signal, and converting the brightness signals into Cartesian coordinates. The B-mode image generator 4 consecutively performs this process for each sub-frame, and outputs cross-sectional images generated as a result to the B-mode image acquirer 51 of the B-mode image processor 5. Specifically, the B-mode image generator 4 performs the brightness conversion by executing processing such as envelope detection, logarithmic compression, and so on on an acoustic line signal. A B-mode image signal is generated by converting the resulting brightness signal into Cartesian coordinates. That is, the B-mode image signal represents the intensity of ultrasound reception signals as brightness.

The B-mode sub-frame image signals generated by the B-mode image generator 4 is transmitted to the B-mode image acquirer 51 in chronological order for every sub-scan performed.

4. B-Mode Image Processor 5

The B-mode image processor 5 is made up of a B-mode image acquirer 51 and a B-mode image compounder 52.

(4.1) B-Mode Image Acquirer 51

The B-mode image acquirer 51 is a circuit equipped with a buffer storing a B-mode sub-frame image signal transmitted chronologically for each sub-scan performed, taking the B-mode image signal generated by the B-mode image generator 4 as input.

(4.2) B-Mode Image Compounder 52

The B-mode image compounder 52 is a circuit generating a B-mode frame image signal resulting from spatial compounding by reading the B-mode sub-frame image signals from the B-mode image acquirer 51 acquired through sub-scans, and by compounding the B-mode sub-frame image signals by using a method of averaging overlapping portions of B-mode image signals acquired from the same position of the subject body, similarly to the depiction provided in FIG. 20C for the conventional ultrasound diagnostic device 10X. The B-mode frame image signal resulting from spatial compounding is output to the enhancement processor 6.

Here, the term frame refers to a unit of signal in which one unit of required information for constructing one cross-sectional image is collected. In the present Embodiment, a frame indicates a unit of acoustic line signal into which one unit of required information for constructing one cross-sectional image is collected, or a unit of B-mode image signal that has been processed to construct a B-mode image based on the acoustic line signal into which the one unit is collected, or to one B-mode image constructed in accordance with the B-mode image signal into which the one unit is collected.

Also, the relationship between a frame and a sub-frame is such that a plurality of B-mode sub-frame image signals are obtained from the sub-scans at different steering angles, and the B-mode sub-frame image signals are compounded into one B-mode frame image signal covering all steering angle using spatial compounding.

Additionally, in the present document, the term reception signal (or ultrasound reception signal) may refer to the B-mode image signal or the acoustic line signal, each of which serving as the basis for generating the B-mode image signal.

5. Enhancement Processor 6

The enhancement processor 6 includes a sub-frame enhancement map creator 62, a B-mode image enhancer 63, a sub-frame enhancement map buffer 64, and a frame enhancement map compounder 65.

(5.1) Sub-Frame Enhancement Map Creator 62

The sub-frame enhancement map creator 62 is a circuit that detects a motion amount of the subject body in the B-mode sub-frame image signal using a frame difference between B-mode sub-frame image signals, creates a sub-frame enhancement map such that a greater enhancement amount is applied to a greater motion amount in the B-mode image signal, and outputs the resulting map to the sub-frame enhancement map buffer 64.

Specifically, the sub-frame enhancement map creator 62 computes a frame difference by reading at least two B-mode sub-frame image signals from the B-mode image acquirer 51, including a current sub-frame and a sub-frame acquired prior to the current sub-frame. The frame enhancement map is created such that the greater the frame difference, the greater the enhancement amount applied to a pixel region identical to the current B-mode sub-frame image signal.

The sub-frame enhancement map created by the sub-frame enhancement map creator 62 is transmitted to the sub-frame enhancement map buffer 64 chronologically each time the sub-scan is performed.

(5.2) Sub-Frame Enhancement Map Buffer 64

The sub-frame enhancement map buffer 64 is a circuit equipped with a buffer storing the sub-frame enhancement map transmitted chronologically for every sub-scan, taking the sub-frame enhancement map generated by the sub-frame enhancement map creator 62 as input.

(5.3) Frame Enhancement Map Compounder 65

The frame enhancement map compounder 65 is a circuit using spatial compounding to perform compounding of the sub-frame enhancement maps making up a frame, thus creating a frame enhancement map. Specifically, the frame enhancement map compounder 65 acquires the sub-frame enhancement map obtained in each sub-scan from the sub-frame enhancement map buffer 64, generates the frame enhancement map by performing compounding using averaging of the overlapping portions of the sub-frame enhancement maps, and outputs the resulting map to the B-mode image enhancer 63. The frame enhancement map generation is performed for each ultrasound scan.

(5.4) B-Mode Image Enhancer 63

The B-mode image enhancer 63 is a circuit acquiring the B-mode frame image signal from the B-mode image compounder 52, acquiring the frame enhancement map from the frame enhancement map compounder 65, and applying enhancement processing to the B-mode frame image signal in accordance with the frame enhancement map. Here, the B-mode image enhancer 63 applies the enhancement processing to the B-mode image signal so that a greater enhancement amount amplifies the brightness of a reception signal from a pixel region (a pixel region reception signal). The enhancement-applied B-mode frame image signal is then output to the display controller 7.

6. Display Controller 7

The display controller 7 is a circuit displaying the B-mode image on the display apparatus 8, which is connected externally, in accordance with the enhancement-applied B-mode frame image signal, which is obtained by spatial compounding.

According to the above-described configuration, the B-mode image compounder 52, the frame enhancement map compounder 65, and the B-mode image enhancer 63 form an enhancement-applied B-mode image generator S.

<Operations>

Figure 2:
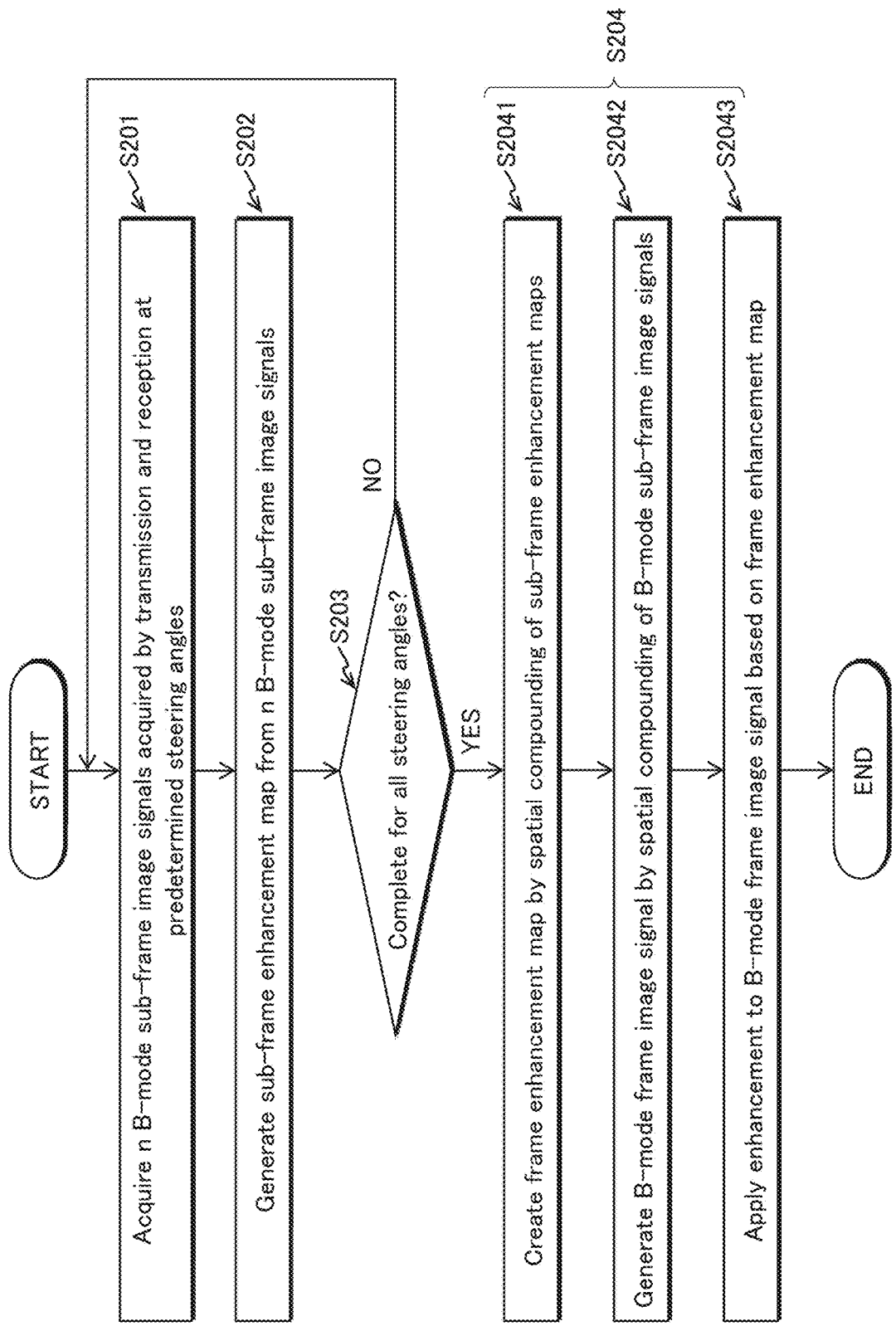
FIG. 2 is a flowchart describing operations of the ultrasound diagnostic device 10 pertaining to Embodiment 1.

The operations of the ultrasound diagnostic device 10, configured as described above, are described next. FIG. 2 is a flowchart describing the operations of the ultrasound diagnostic device 10 pertaining to Embodiment 1.

1. Step S201

In step S201, a plurality (n) of B-mode sub-frame image signals are acquired by transmission and reception performed at predetermined steering angles. Specifically, the ultrasound probe 1 is disposed at the subject body skin surface. The ultrasound transmitter and receiver 2 then generates the acoustic line signal by performing a transmission process of transmitting an ultrasound into the subject body from the ultrasound probe 1, and a reception process based on the reflected ultrasound received from the subject body via the ultrasound probe 1. One sub-frame made up of a plurality of acoustic line signals is constructed by performing a sub-scan, including the transmission process and the reception process, being repeatedly performed in a quantity corresponding to the quantity of transducers in the ultrasound probe 1 or the like. The acoustic line signals for the sub-frame constructed for each sub-scan is then output to the B-mode image generator 4. The B-mode image generator 4 takes the acoustic line signals for the sub-frame as input, generates a B-mode sub-frame image signal, and outputs the signal to the B-mode image acquirer 51 in chronological order for each sub-scan.

FIG. 3 describes the operations of the ultrasound diagnostic device 10. As indicated by FIG. 3, reading from the top, sub-scans 1, 2, and 3 are sequentially performed during ultrasound scan 1, and B-mode sub-frame images signals 1, 2, and 3 are obtained in the stated order. Also, subsequently, sub-scans 4, 5, and 6 are sequentially performed during ultrasound scan 2, and B-mode sub-frame images signals 4, 5, and 6 are obtained in the stated order.

2. Step S202

In step S202, a sub-frame enhancement map is created from the plurality (n) of B-mode sub-frame image signals. The sub-frame enhancement map is created by detecting a motion amount of the subject body in a B-mode sub-frame image signal using a frame difference between B-mode sub-frame image signals, such that a greater enhancement amount is applied to the B-mode sub-frame image signal for a greater motion amount.

Specifically, the sub-frame enhancement map creator 62 computes a frame difference by reading at least two B-mode sub-frame image signals from the B-mode image acquirer 51, including a current sub-frame and a sub-frame acquired prior to the current sub-frame. Here, the B-mode sub-frame image signal acquired prior to the current sub-frame is a B-mode sub-frame image signal acquired earlier than the acquisition of the current B-mode sub-frame image signal at the same steering angle as the current B-mode sub-frame image signal. The frame difference is a difference between pixel regions, made up of one or more pixels, acquired at the same position on the subject body in the current B-mode sub-frame image signal and the B-mode sub-frame image signal acquired prior to the current sub-frame. The frame enhancement map is created such that the greater the difference, the greater the enhancement amount applied to the identical pixel region identical in the B-mode sub-frame image signal of the current sub-frame.

In the example depicted in FIG. 3, as read from the top, once sub-scan 4 is performed during ultrasound scan 2, the frame difference (indicated as (4–1) in FIG. 3) is computed between B-mode sub-frame image signal 4 and B-mode sub-frame image signal 1, acquired from sub-scan 1 during ultrasound scan 1. The motion amount in B-mode sub-frame image signal 4 relative to B-mode sub-frame image signal 1 is calculated in accordance with this frame difference. Then, a sub-frame enhancement map (indicated in FIG. 3 and other drawings as sub-frame enhancement map (4–1)) such that the greater the motion amount, the greater the enhancement amount applied to the identical pixel region in the B-mode sub-frame image signal 4.

Similarly, once sub-scan 5 is performed, the frame difference is computed between B-mode sub-frame image signal 5 and B-mode sub-frame image signal 2, acquired from sub-scan 2 during ultrasound scan 1, and a sub-frame enhancement map (5–2) corresponding to B-mode sub-frame image signal 5 is created based on that frame difference.

Further, once sub-scan 6 is performed, the frame difference is computed between B-mode sub-frame image signal 6 and B-mode sub-frame image signal 3, acquired from sub-scan 3 during ultrasound scan 1, and a sub-frame enhancement map (6–3) corresponding to B-mode sub-frame image signal 6 is created based on that frame difference.

These sub-frame enhancement maps are then output to the sub-frame enhancement map buffer 64.

The frame difference is not computed for the sub-scans during ultrasound scan 1 given that no prior sub-frame exists therefor, and the sub-frame enhancement map is thus not created.

3. Step S203

In step S203, a determination is made regarding whether or not the generation of the sub-frame enhancement map is complete for the plurality (n) of B-mode sub-frame image signals pertaining to all steering angles. When the process is complete for all steering angles, the process advances to the next step.

4. Enhancement-Applied B-Mode Image Generation Step S204

The enhancement-applied B-mode image generation step S204 includes sub-steps S2041, S2042, and S2043.

(4.1) Sub-Step S2041

In sub-step S2041, the frame enhancement map is created by spatial compounding of the sub-frame enhancement maps. Specifically, the frame enhancement map compounder 65 acquires the plurality (n) of sub-frame enhancement maps obtained in the sub-scans for all steering angles from the sub-frame enhancement map buffer 64, generates the frame enhancement map by averaging the overlapping portions of the sub-frame enhancement maps, and outputs the resulting map to the B-mode image enhancer 63. The frame enhancement map generation is performed once for each ultrasound scan.

In the example indicated in FIG. 3, the frame enhancement map (indicated as frame enhancement map (4+5+6-1-2-3) in FIG. 3 and other drawings) is generated by compounding three sub-frame enhancement maps (4-1), (5-2), and (6-3), once sub-scan 6 has been completed during ultrasound scan 2. The frame enhancement map is created as ultrasound scans 3 and 4 are performed, subsequently, in descending order in FIG. 3.

(4.2) Sub-Step S2042

In sub-step S2042, a frame reception signal is generated by spatial compounding of the B-mode sub-frame image signals. Specifically, the B-mode image compounder 52 acquires the B-mode sub-frame image signals from the B-mode image acquirer 51 and generates a B-mode frame image signal by averaging the overlapping portions of the B-mode image signals acquired at the same position on the subject body. This B-mode frame image signal is output to the enhancement processor 6.

In the example depicted in FIG. 3, B-mode frame image signal (4+5+6) is generated by compounding B-mode sub-frame image signals 4, 5, and 6, once sub-scan 6 has been performed during ultrasound scan 2. The frame enhancement map is created as ultrasound scans 3 and 4 are performed, subsequently, in descending order in FIG. 3.

(4.3) Sub-Step S2043

In sub-step S2043, enhancement is applied to the B-mode frame image signal in accordance with the frame enhancement map. Specifically, the B-mode image enhancer 63 acquires the B-mode frame image signal from the B-mode image compounder 52, acquires the frame enhancement map from the frame enhancement map compounder 65, and applies enhancement processing to the B-mode frame image signal in accordance with the frame enhancement map. Here, the B-mode image enhancer 63 applies the enhancement processing to the B-mode image signal so that a greater enhancement amount amplifies the brightness of a corresponding pixel region reception signal. For example, the B-mode image enhancer 63 may multiply an enhancement amount in the frame enhancement map corresponding to a pixel region reception signal with the pixel region reception signal in the frame reception signal, or the B-mode image enhancer 63 may add the enhancement amount in the frame enhancement map corresponding to the pixel region reception signal to the pixel region reception signal, thereby applying enhancement to the frame image signal pixel region by pixel region.

In the example of FIG. 3, enhancement is applied to B-mode frame image signal (4+5+6), acquired once sub-scan 6 has been performed during ultrasound scan 2, in accordance with frame enhancement map (4+5+6-1-2-3). An enhancement-applied B-mode frame image signal (4+5+6)×(k) is created as ultrasound scans 3 and 4 are performed, subsequently, in descending order in FIG. 3.

The enhancement-applied B-mode image generation step S204 is completed by performing the above-described sub-steps S2041, S2042, and S2043.

The enhancement-applied B-mode frame image signal is output to the display controller 7, and a B-mode image based on the enhancement-applied B-mode frame image signal is displayed by the display apparatus 8. A display process is then performed by updating the B-mode image for each ultrasound scan that occurs.

<Puncture Needle Visibility>

Figure 4A:
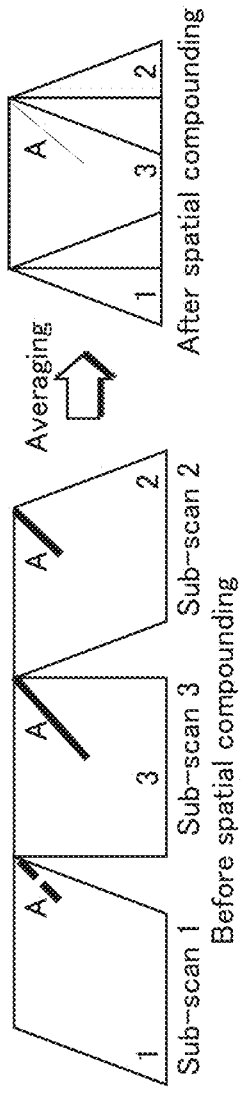
FIGS. 4A through 4E schematically describe a puncture needle enhancement operation performed by the ultrasound diagnostic device 10 pertaining to Embodiment 1.
Figure 4B:
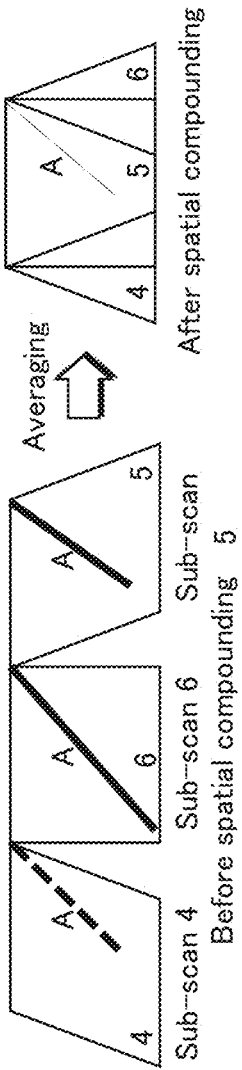

The effect of improving the visibility of the puncture needle provided by the ultrasound diagnostic device 10 pertaining to Embodiment 1 is described next, with reference to the drawings. FIGS. 4A through 4E schematically describe a puncture needle enhancement operation performed by the ultrasound diagnostic device 10 pertaining to Embodiment 1. FIG. 4A schematically represents B-mode sub-frame image signals 1, 2, and 3 acquired from sub-scans 1, 2, and 3 of FIG. 3, and B-mode frame image signal (1+2+3) generated by performing compounding thereof. FIG. 4B schematically represents B-mode sub-frame image signals 4, 5, and 6 acquired from sub-scans 4, 5, and 6 of FIG. 3, and B-mode frame image signal (4+5+6) generated by performing compounding thereof. Again, the puncture needle (labeled A in FIG. 21) is inserted from the upper right to the lower right in the drawings, similar to the example indicated by the arrows in FIG. 21.

As such, in sub-scan 1, the angle between the ultrasound beam emission direction and the puncture needle is small. This results in low visibility of the puncture needle, which is barely noticeable in B-mode sub-frame image signal 1. Conversely, in B-mode sub-frame image signals 2 and 3, respectively obtained from sub-scan 2 and sub-scan 3, the puncture needle is clearly indicated. Then, in the B-mode frame image signal obtained through compounding by averaging B-mode sub-frame image signals 1, 2, and 3, the visibility of the puncture needle is relatively low in comparison to B-mode sub-frame image signals 2 and 3. Likewise, in B-mode frame image signal (4+5+6), the visibility of the puncture needle is relatively low in comparison to B-mode sub-frame image signals 5 and 6.

Figure 4C:
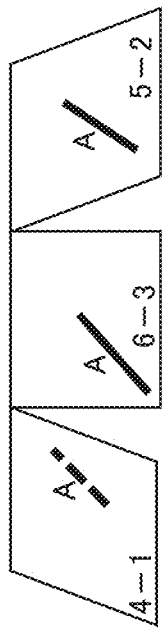
Figure 4D:
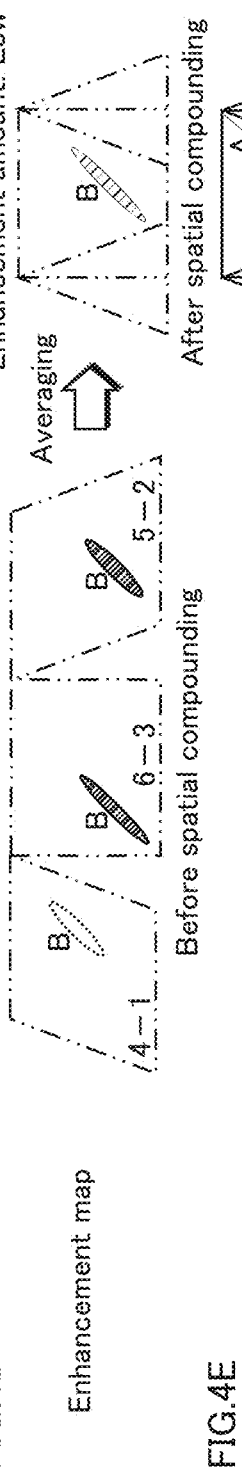

FIG. 4C schematically represents the mapping of motion amounts that are obtained by computing the frame difference between B-mode sub-frame image signals 4, 5, and 6 and B-mode sub-frame image signals 1, 2, and 3, respectively. FIG. 4D schematically represents the sub-frame enhancement maps calculated from the motion amounts such that the greater the motion amount, the greater the enhancement amount, and the frame enhancement map obtained by performing compounding thereof.

B-mode sub-frame image signals 4 and 1 are both obtained under conditions in which the angle between the puncture needle and the ultrasound beam is small, such that the puncture needle is not clearly indicated and the puncture needle is thus barely noticeable. As such, the puncture needle is barely detected using the motion amount obtained from the frame difference between B-mode sub-frame image signals 4 and 1. Enhancement amount B applied to the puncture needle in sub-frame enhancement map (4-1) based on this frame difference is thus extremely small.

Conversely, enhancement amount B applied to the puncture needle is comparatively great in sub-frame enhancement map (5-2), obtained by detecting the position of the puncture needle from the motion amount derived from the frame difference between B-mode sub-frame image signals 5 and 2 and creating the enhancement map based on the frame difference. The same applies to sub-frame enhancement map (6-3), created from B-mode sub-frame image signals 6 and 3.

Figure 4E:

As such, in frame enhancement map (4+5+6-1-2-3), compounded by averaging the three sub-frame enhancement maps, enhancement amount B applied to the puncture needle is small in comparison to sub-frame enhancement maps (5-2) and (6-3), but greater than sub-frame enhancement map (4-1). As a result, and as depicted in FIG. 4E, the degree of enhancement on the puncture needle in the enhancement-applied B-mode frame image signal (4+5+6) is the average of the enhancement levels of the sub-frame enhancement maps.

Figure 5:
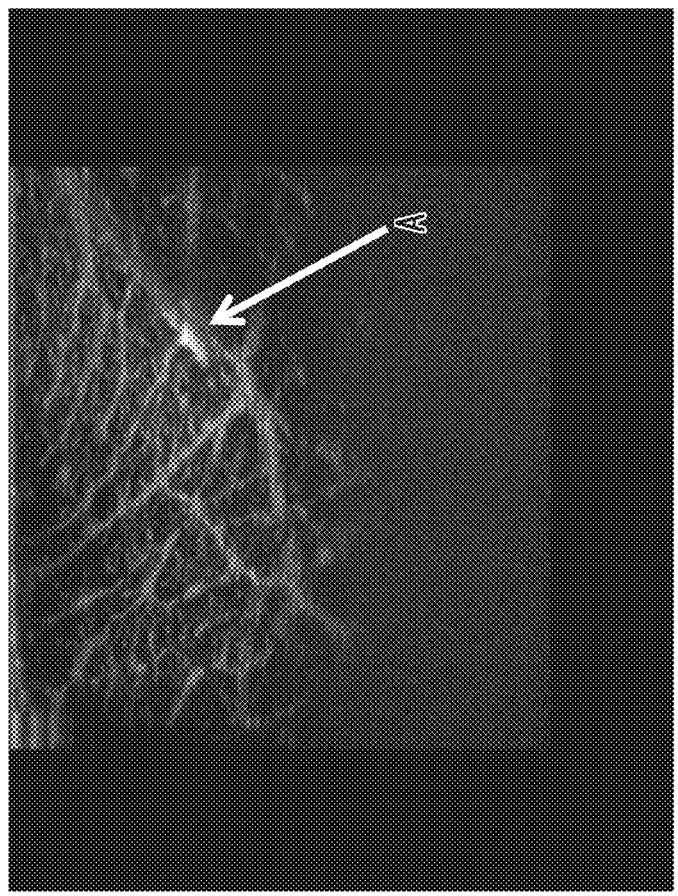
FIG. 5 depicts a B-mode image with enhancement applied to a puncture needle as obtained by the ultrasound diagnostic device 10 pertaining to Embodiment 1.

The inventors evaluated the effect of puncture needle enhancement performed by the ultrasound diagnostic device 10 pertaining to Embodiment 1 using the B-mode images. FIG. 5 depicts a B-mode image with enhancement applied to the puncture needle as obtained by the ultrasound diagnostic device 10 pertaining to Embodiment 1. As illustrated by FIG. 5, in the enhancement-applied B-mode frame image signal, puncture needle A is sufficiently visible, with a top thereof being particularly enhanced.

Figure 6:
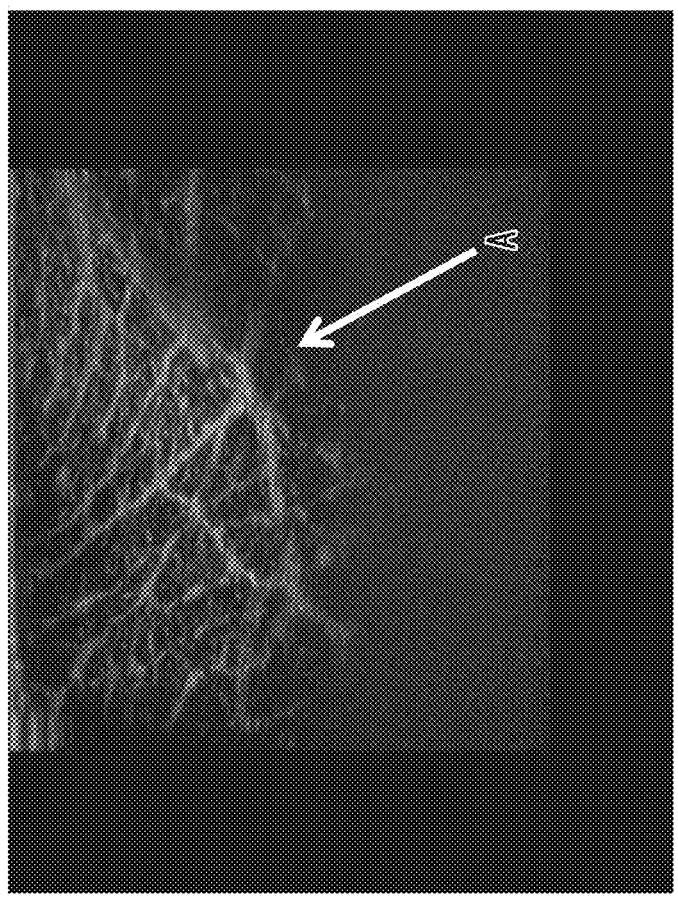
FIG. 6 depicts a B-mode image acquired from an ultrasound diagnostic device 10Y considered by the inventors as a comparative example.

As described above, the puncture needle enhancement processing applied to the B-mode image compounded using spatial compounding by the ultrasound diagnostic device 10Y considered by the inventors may produce an extremely small enhancement amount for the puncture needle in each cycle of sub-scan steering angle change when the frame enhancement map is created using the frame difference between B-mode frame image signals. FIG. 6 depicts a B-mode image acquired from the above-described ultrasound diagnostic device 10Y considered by the inventors as a comparative example. Here, puncture needle A is barely noticeable in the B-mode frame image signal.

In contrast, the ultrasound diagnostic device 10 pertaining to the present Embodiment produces, as illustrated by FIG. 5, sufficient visibility for puncture needle A with the tip thereof being enhanced in the enhancement-applied B-mode frame image signal that is generated, regardless of the steering angle in the sub-scans used for spatial compounding.

(Conclusion)

As described above, the ultrasound diagnostic device pertaining to Embodiment 1 generates a frame reception signal by compounding a plurality of sub-frame reception signals acquired from a subject body through an ultrasound probe. The sub-frame reception signals are each generated through one of a plurality of sub-scans composing an ultrasound scan, and between the sub-scans, a range in the subject body that is scanned differs due to a different one of a plurality of ultrasound beam steering angles being used. The ultrasound diagnostic device has a control circuit, the control circuit including: a reception signal acquirer acquiring the sub-frame reception signals; a sub-frame enhancement map creator creating a plurality of sub-frame enhancement maps, each corresponding to one of the sub-frame reception signals, the creating of each of the sub-frame enhancement maps being performed by calculating, for a pixel region reception signal included in a corresponding one of the sub-frame reception signals, an enhancement amount in accordance with a characteristic value calculated based on the pixel region reception signal, the pixel region reception signal corresponding to a pixel region composed of one or more pixels; and an enhancement-applied reception signal generator generating an enhancement-applied frame reception signal by compounding pixel region reception signals included in the sub-frame reception signals based on pixel region positions, while taking into account the enhancement amount included in at least one of the sub-frame enhancement maps.

According to this configuration, the ultrasound diagnostic device 10 improves the visibility of the puncture needle during an ultrasound image diagnostic using spatial compounding. Thus, a more user-friendly ultrasound image processing method and an ultrasound diagnostic device using the method are provided.

(Variation 1)

In Embodiment 1, the frame enhancement map compounder 65 creates the frame enhancement map by averaging the sub-frame enhancement maps from a plurality of sub-frame reception signals. However, the frame enhancement map compounder may also change the method of compounding the frame enhancement map as appropriate, provided that a frame enhancement map is created by compounding the sub-frame enhancement maps from the sub-frame reception signals.

The ultrasound diagnostic device pertaining to the present Variation further amplifies the enhancement amount such that the enhancement amount obtained by averaging the sub-frame enhancement maps for the sub-frame reception signals reaches or approaches an upper limit when equal to or greater than a predetermined value. Here, the enhancement amount is said to approach the upper limit when the enhancement amount is equal to or greater than a predetermined value and thus is increased to be asymptotic to an upper limit value.

Figure 7:
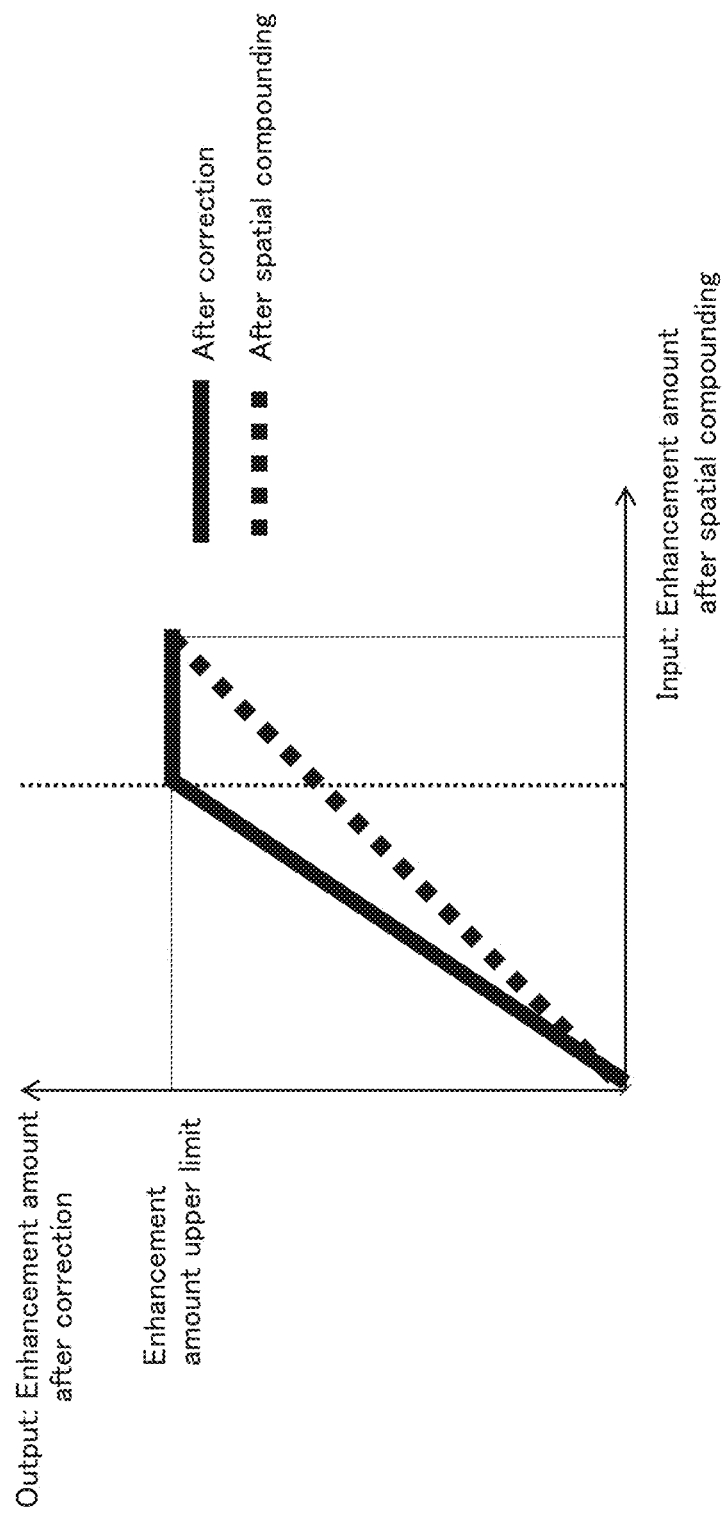
FIG. 7 schematically describes a puncture needle enhancement operation performed by an ultrasound diagnostic device pertaining to Variation 1 of Embodiment 1.

FIG. 7 schematically describes a puncture needle enhancement operation performed by the ultrasound diagnostic device pertaining to Variation 1 of Embodiment 1. As indicated in FIG. 7, the frame enhancement map compounder 65 of the ultrasound diagnostic device pertaining to Variation 1 performs a predetermined amplification process on the enhancement amount, taken as input after spatial compounding, and outputs the result to the B-mode image enhancer 63. When the enhancement amount is equal to or greater than the predetermined value, then the value of the upper limit is output instead of the enhancement amount after the enhancement processing, even in cases where the enhancement amount input after spatial compounding is greater. Here, the processing applied near the upper limit may be any processing smoothly causing enhancement amounts to approach the upper limit, for example logarithmic conversion.

Figure 8:
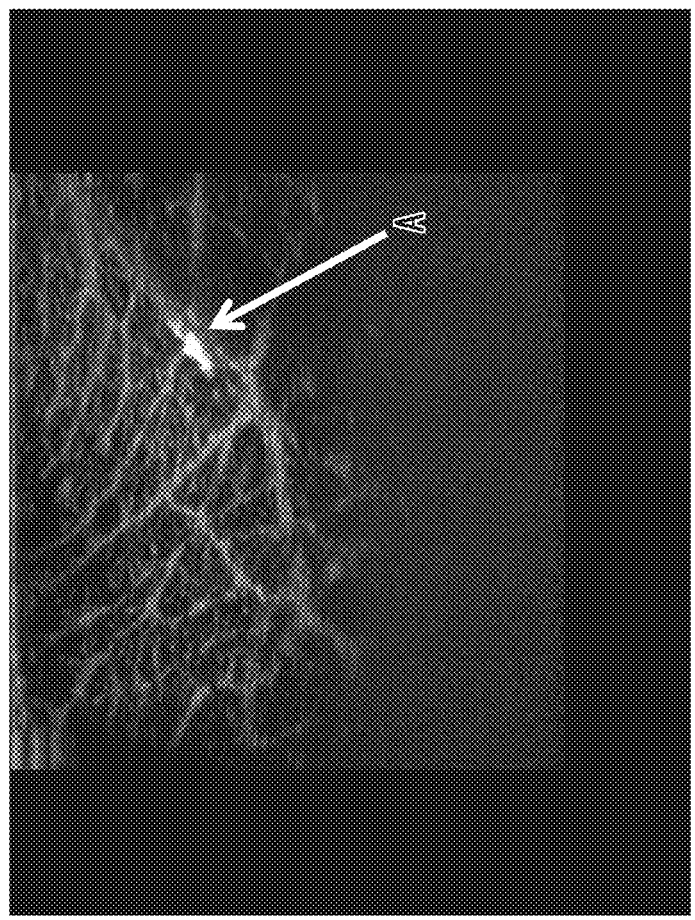
FIG. 8 depicts a B-mode image with enhancement applied to the puncture needle as obtained by the ultrasound diagnostic device pertaining to Variation 1 of Embodiment 1.

FIG. 8 depicts a B-mode image with enhancement applied to the puncture needle as obtained by the ultrasound diagnostic device pertaining to Variation 1 of Embodiment 1. In comparison to the B-mode image pertaining to Embodiment 1 using the averaging process as illustrated in FIG. 5, Variation 1 clearly displays the tip of the puncture needle through amplification.

According to this configuration, even when the enhancement amount in one or more of the sub-frame enhancement maps is small, a predetermined amplification process is applicable to the enhancement amount of the frame enhancement map, which increases the enhancement amount on the puncture needle in the frame enhancement map. Amplifying the enhancement amount in the frame enhancement map is effective in cases where the puncture needle is not clearly indicated in one or more of the B-mode sub-frame image signals.

In the above-described Variation 1, the aforementioned predetermined value, which is the threshold for increasing the enhancement amount to reach or approach the upper limit, may be determined according to the quantity of sub-frames. Also, the predetermined value may increase as the quantity of sub-frames used in compounding increases. The quantity of sub-frames used in compounding determines the ratio of sub-frame enhancement maps created with a small enhancement amount on the puncture needle to total sub-frame enhancement maps. Setting the predetermined value according to this ratio thus enables greater enhancement results.

<Embodiment 2>

In Embodiment 1, the frame enhancement map compounder 65 creates the frame enhancement map by averaging the sub-frame enhancement maps from a plurality of sub-frame reception signals, with equal weighting for all of the sub-frame enhancement maps. Embodiment 2 differs from Embodiment in that the frame enhancement map compounder 65 creates the frame enhancement map by compounding the sub-frame enhancement maps in accordance with a correction condition pertaining to the steering angle for the sub-scan in which each sub-frame reception signal is acquired. Aside from the frame enhancement map compounder 65, the configuration of the components are identical to those of Embodiment 1, and explanations thereof are therefore omitted.

(Configuration)

1. Method 1

Figure 9:
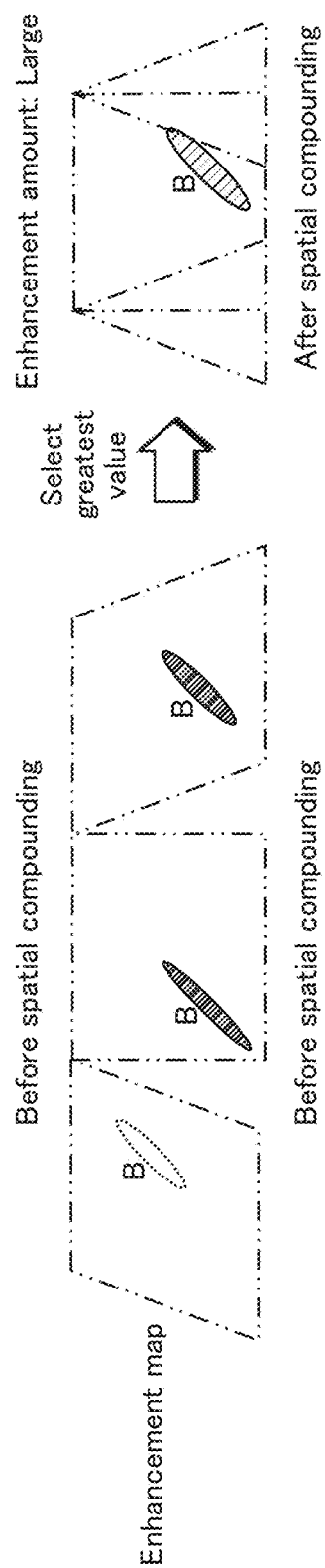
FIG. 9 schematically illustrates a frame enhancement map compounding method according to a first method employed by an ultrasound diagnostic device pertaining to Embodiment 2.

FIG. 9 schematically illustrates a frame enhancement map compounding method according to a first method employed by the ultrasound diagnostic device pertaining to Embodiment 2. As indicated in FIG. 9, according to the first method, the frame enhancement map compounder 65 creates the frame enhancement map by compounding the sub-frame enhancement maps in accordance with a correction condition of using, as the frame enhancement map, a sub-frame enhancement map including a greatest enhancement value, among the sub-frame enhancement maps. The greatest enhancement amount is an enhancement amount applied to a pixel region, which includes one or more pixels. That is, the frame enhancement map compounder 65 selects, as the frame enhancement map, one sub-frame enhancement map in which a greatest enhancement amount B is applied to the pixel region among the sub-frame enhancement maps in which the enhancement amount B is applied to the pixel region. According to this configuration, the effect of any sub-frame enhancement map in which a small enhancement amount B is applied to the puncture needle is removed. This enables the enhancement amount in the frame enhancement map to be increased by creating the frame enhancement map only from a sub-frame enhancement map in which a great enhancement amount B is applied to the puncture needle.

Figure 10:
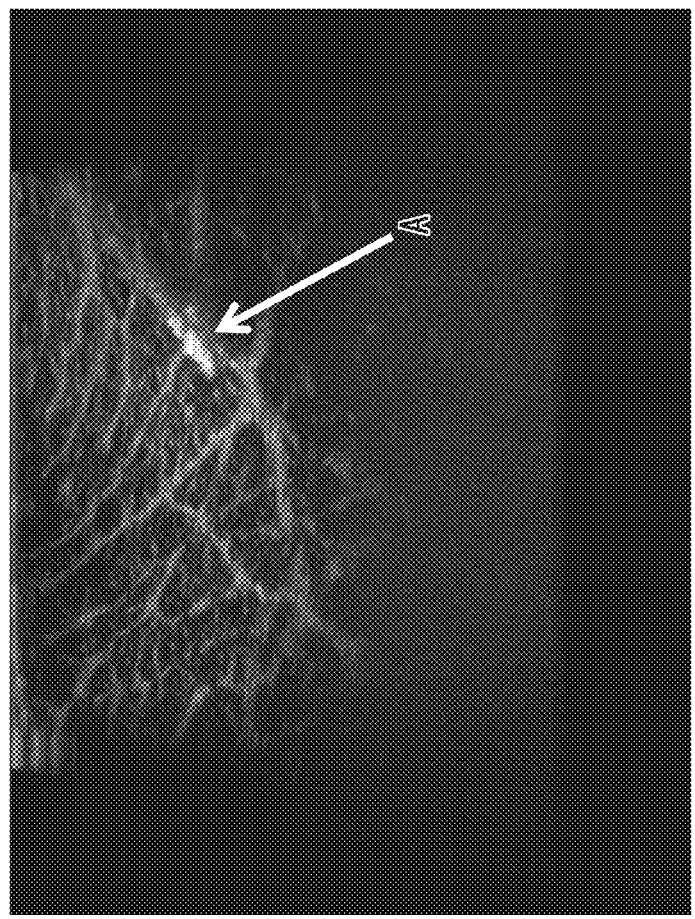
FIG. 10 depicts a B-mode image with enhancement applied to the puncture needle as obtained by the ultrasound diagnostic device pertaining to Embodiment 2.

FIG. 10 depicts a B-mode image with enhancement applied to the puncture needle as obtained using the first method. According to the first method, due to a maximum value being selected, the tip of the puncture needle is displayed more clearly in comparison to the example depicted in FIG. 5 for Embodiment 1.

2. Method 2

Figure 11:
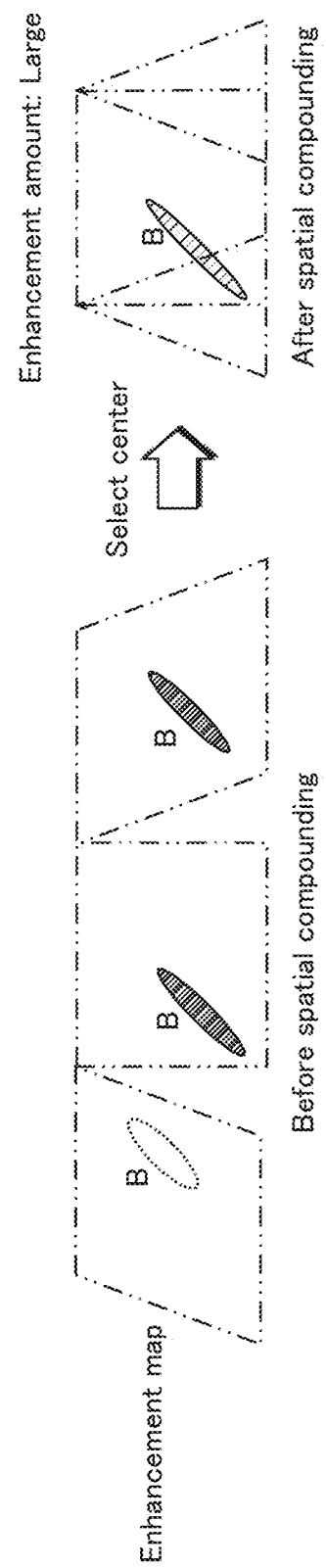
FIG. 11 schematically illustrates a frame enhancement map compounding method according to a second method employed by the ultrasound diagnostic device pertaining to Embodiment 2.

FIG. 11 schematically illustrates a frame enhancement map compounding method according to a second method. As depicted in FIG. 11, according to the second method, the frame enhancement map compounder 65 creates the frame enhancement map by compounding the sub-frame enhancement maps according to a correction condition of using, as the frame enhancement map, a sub-frame enhancement maps based on a sub-scan corresponding to a steering angle around a center, among the sub-frame enhancement maps. In many cases, the B-mode sub-frame image acquired from the sub-scan performed with a steering angle around the center among the sub-scans displays the puncture needle with a clarity that is the average value across all steering angles. According to this configuration, creating the frame enhancement map from a sub-frame enhancement map having the average enhancement amount B applied to the puncture needle enables the enhancement amount in the frame enhancement map to be raised to the average.

Figure 12:
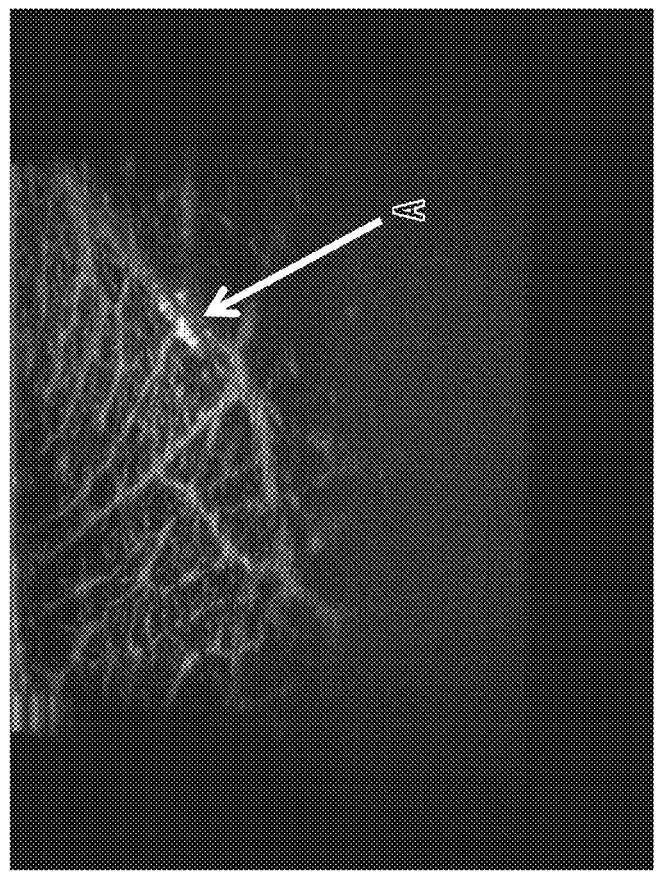
FIG. 12 depicts a B-mode image with enhancement applied to the puncture needle as obtained by the second method used by the ultrasound diagnostic device pertaining to Embodiment 2.

FIG. 12 depicts a B-mode image with enhancement applied to the puncture needle as obtained using the second method. Although less clarity is provided than the first method, the tip of the puncture needle is displayed more clearly in comparison to the example depicted in FIG. 5 for Embodiment 1.

3. Method 3

Figure 13:
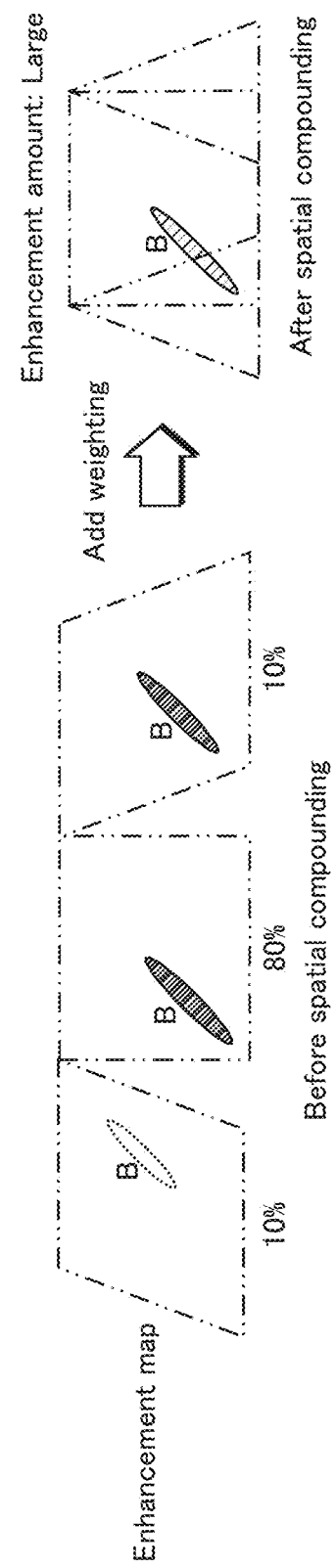
FIG. 13 schematically illustrates a frame enhancement map compounding method according to a third method employed by the ultrasound diagnostic device pertaining to Embodiment 2.

FIG. 13 schematically illustrates a frame enhancement map compounding method according to a third method. As depicted in FIG. 13, according to the third method, the frame enhancement map compounder 65 creates the frame enhancement map in accordance with a correction condition of providing greater weight to a sub-frame enhancement map based on a sub-scan corresponding to a steering angle around a center, among the sub-frame enhancement maps, than a sub-frame enhancement map based on a sub-scan corresponding to a steering angles not around the center, among the sub-frame enhancement maps, and the weighting of the sub-frame enhancement maps is reflected by addition or multiplication. As described above, in many cases, the B-mode sub-frame image acquired from the sub-scan performed with a steering angle around the center among the sub-scans displays the puncture needle with a clarity that is the average across all steering angles. Thus, this configuration allows increasing the enhancement amount B of the frame enhancement map by increasing the weighting of the sub-frame enhancement map acquired from the sub-scan around the center, while maintaining consideration of the sub-frame enhancement maps acquired from the sub-scans performed at other steering angles.

Figure 14:
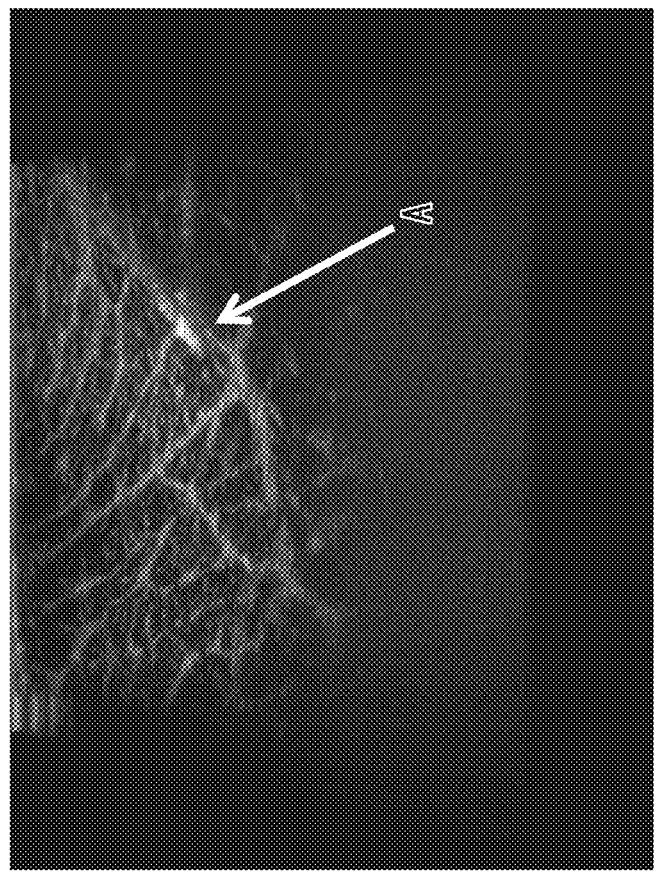
FIG. 14 depicts a B-mode image with enhancement applied to the puncture needle as obtained by the third method used by the ultrasound diagnostic device pertaining to Embodiment 2.

FIG. 14 depicts a B-mode image with enhancement applied to the puncture needle as obtained using the third method. A similar amount of clarity as the second method is provided for the puncture needle, and the tip of the puncture needle is displayed more clearly in comparison to the example depicted in FIG. 5 for Embodiment 1.

4. Method 4

Figure 15:
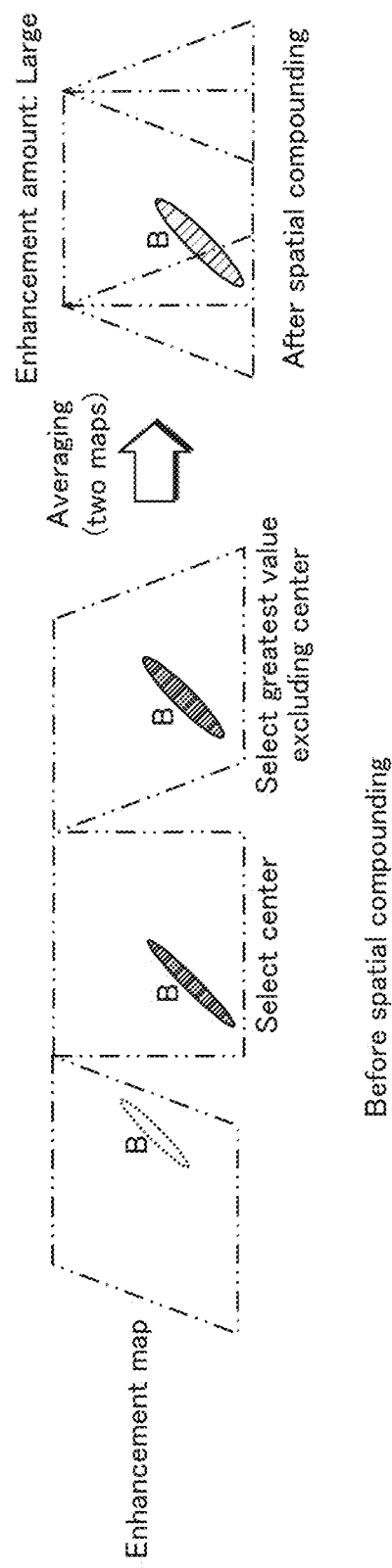
FIG. 15 schematically illustrates a frame enhancement map compounding method according to a fourth method employed by the ultrasound diagnostic device pertaining to Embodiment 2.

FIG. 15 schematically illustrates a frame enhancement map compounding method according to a fourth method. As depicted in FIG. 15, according to the fourth method, the frame enhancement map compounder 65 creates the frame enhancement map in accordance with a correction condition of compounding a sub-frame enhancement map based on a sub-scan corresponding to a steering angle around a center, among the sub-frame enhancement maps, and a sub-frame enhancement map that is based on a sub-scan corresponding to a steering angle not around the center and that has a relatively great total enhancement value, among the sub-frame enhancement maps, the total enhancement value being a total of enhancement values in a sub-frame enhancement map. According to this configuration, the frame enhancement map is compounded from a sub-frame enhancement map in which the total enhancement amount applied to the puncture needle is relatively great, and the sub-frame enhancement map from a steering angle around the center among the steering angles. This enables the enhancement amount B in the frame enhancement map to be more reliably increased.

Also, in the above method, the sub-frame enhancement map based on the sub-scan from a steering angle around the center among the steering angles may be omitted from compounding. Instead, at least one sub-frame enhancement map among sub-frame enhancement maps based on a sub-scan other than the sub-scan from the steering angle around the center among the steering angles in which the total enhancement amount applied to the pixel region therein is relatively great may be used as the frame enhancement map. This approach also enables the enhancement amount in the frame enhancement map to be reliably increased.

5. Method 5

Figure 16:
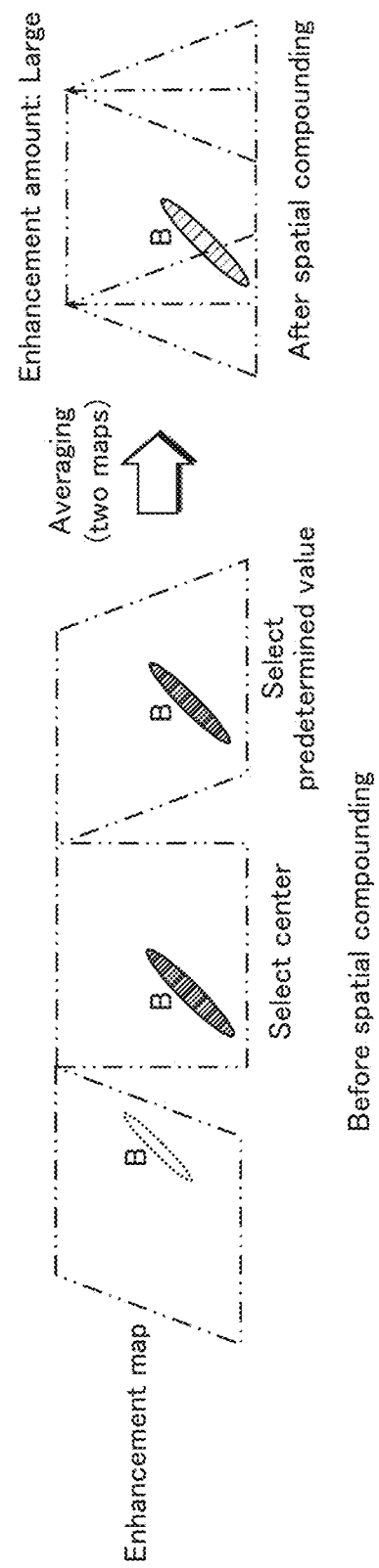
FIG. 16 schematically illustrates a frame enhancement map compounding method according to a fifth method employed by the ultrasound diagnostic device pertaining to Embodiment 2.

FIG. 16 schematically illustrates a frame enhancement map compounding method according to a fifth method. As depicted in FIG. 16, according to the fifth method, the frame enhancement map compounder 65 creates the frame enhancement map in accordance with a correction condition of compounding a sub-frame enhancement map based on a sub-scan corresponding to a steering angle around a center, among the sub-frame enhancement maps, and a sub-frame enhancement map based on a sub-scan corresponding to a predetermined steering angle that is not around the center, among the sub-frame enhancement maps.

In many cases, the puncture needle punctures the subject body through a guide in a puncture adapter affixed to the ultrasound probe. As such, the puncture direction of the puncture needle into the subject body relative to the transducer array direction of the ultrasound probe is known in advance. Accordingly, at least one sub-frame enhancement map acquired from a sub-scan performed at a steering angle that is nearly perpendicular to the angle between the puncture needle and the ultrasound beam is definable in advance. Using such a sub-frame enhancement map in compounding the frame enhancement map enables the enhancement amount in the frame enhancement map to be increased simply and reliably. Also, creating the frame enhancement map by compounding with the sub-frame enhancement map based on the sub-scan from the steering angle around the center among the steering angles enables the enhancement amount in the frame enhancement map to be more reliably increased.

Also, in the above method, the sub-frame enhancement map based on the sub-scan based on the steering angle around the center among the steering angles may be omitted from compounding. Instead, at least one sub-frame enhancement map among sub-frame enhancement maps based on a sub-scan other than the sub-scan based on the steering angle around the center among the steering angles and taken at a predetermined steering angle a may be used as the frame enhancement map. This approach also enables the enhancement amount in the frame enhancement map to be reliably increased.

(Conclusion)

As described above, the ultrasound diagnostic device pertaining to Embodiment 2 has the frame enhancement map compounder 65 create the frame enhancement map by compounding the sub-frame enhancement maps in accordance with a correction condition pertaining to the steering angle for the sub-scan in which each sub-frame reception signal is acquired. According to this configuration, the enhancement amount applied to the puncture needle is increased in the frame enhancement map, thus enabling increased visibility for the puncture needle during an ultrasound image diagnostic using spatial compounding.

<Embodiment 3>

In Embodiment 1, enhancement is applied to the B-mode frame image signal by creating a plurality of sub-frame enhancement maps for a plurality of B-mode sub-frame image signals, each obtained by calculating an enhancement amount for a B-mode image signal of a pixel region in accordance with a motion amount calculated from a corresponding pixel region reception signal in each of the B-mode sub-frame image signals.

However, the sub-frame enhancement maps need only have enhancement amounts mapped with respect to the sub-frame image signals, each obtained by calculating an enhancement amount for an image signal of a pixel region in accordance with a characteristic value calculated from a corresponding pixel region reception signal in the sub-frame reception signals. The method of compounding the frame enhancement map may be adjusted as appropriate.

An ultrasound diagnostic device 10A pertaining to Embodiment 3 calculates an enhancement amount for an acoustic line signal of a pixel region, creates a plurality of sub-frame enhancement maps, each corresponding to one of a plurality of sub-frame acoustic line signals, and applies enhancement to a frame acoustic line signal. The enhancement amount for the acoustic line signal of the pixel region is calculated by using a difference (an amount of change) between the acoustic line signal of the pixel region and an acoustic line signal of a pixel region near the pixel region as a characteristic value calculated from the acoustic line signal of the pixel region, which is composed of one or more pixels.

(Configuration)

Figure 17:
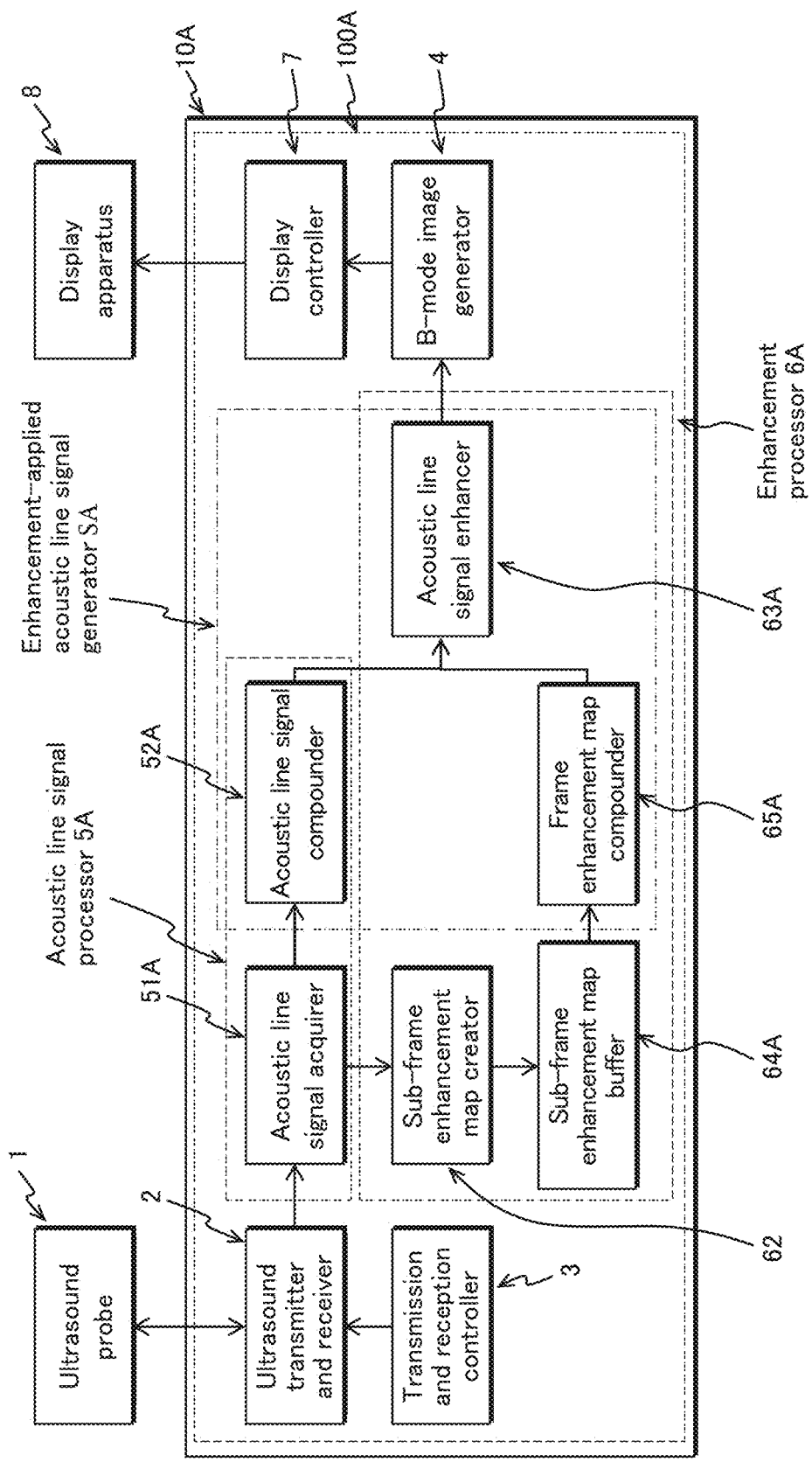
FIG. 17 is a functional block diagram of an ultrasound diagnostic device 10A pertaining to Embodiment 3.

The configuration of the ultrasound diagnostic device 10A is described below. FIG. 17 is a functional block diagram of the ultrasound diagnostic device 10A pertaining to Embodiment 3. The ultrasound diagnostic device 10A is configured from a control circuit 100A that includes an ultrasound transmitter and receiver 2, a transmission and reception controller 3, a B-mode image generator 4, an acoustic line signal image processor 5A, an enhancement processor 6A, and a display controller 7. Among these, with the exception of the configurations of the acoustic line signal processor 5A and the enhancement processor 6A, all components are identical to those of the ultrasound diagnostic device 10 pertaining to Embodiment 1, and explanations thereof are omitted.

1. Acoustic Line Signal Processor 5A

The acoustic line signal processor 5A includes an acoustic line signal acquirer MA and an acoustic line signal compounder 52A.

The acoustic line signal acquirer MA is a circuit taking the acoustic line signals generated by the ultrasound transmitter and receiver 2 as input, and equipped with a buffer storing sub-frame acoustic line signals transmitted in chronological sequence as the sub-scans are performed.

The acoustic line signal compounder 52A is a circuit that reads a sub-frame acoustic line signals acquired in each sub-scan from the acoustic line signal acquirer 51A and, similarly to ultrasound diagnostic device 10, generates a frame acoustic line signal by compounding using an averaging method on overlapping portions of the acoustic line signals at the same position on the subject body. This frame acoustic line signal is output to the enhancement processor 6A.

Also, the relationship between the frame and the sub-frame is such that a plurality of sub-frame acoustic line signals are obtained from each sub-scan at a different steering angle, and the sub-frame acoustic line signals are compounded into one frame acoustic line signal covering all steering angles using spatial compounding.

2. Enhancement Processor 6A

The enhancement processor 6A includes a sub-frame enhancement map creator 62A, an acoustic line signal enhancer 63A, a sub-frame enhancement map buffer 64A, and a frame enhancement map compounder 65A.

The sub-frame enhancement map creator 62A is a circuit that detects intensity of an acoustic line signal of a pixel region within the sub-frame from the sub-frame acoustic line signal and calculates a difference in intensity between the acoustic line signal of the pixel region and the acoustic line signal of another pixel region in the vicinity of the pixel region. The sub-frame enhancement map creator 62A creates the sub-frame enhancement map under a condition such that the greater the difference, the greater the enhancement amount for the acoustic line signal of the pixel region, and outputs the sub-frame enhancement map to the sub-frame enhancement map buffer 64A.

The sub-frame enhancement map buffer 64A is a circuit equipped with a buffer storing the sub-frame enhancement map transmitted chronologically for every sub-scan.

The frame enhancement map compounder 65A is a circuit creating a frame enhancement map each time an ultrasound scan is performed, and outputting the frame enhancement map to the acoustic line signal enhancer 63A. The frame enhancement map compounder 65A creates the frame enhancement map by compounding the sub-frame enhancement maps through spatial compounding of averaging overlapping portions.

The acoustic line signal enhancer 63A is a circuit applying enhancement to the frame acoustic line signal in accordance with the frame enhancement map and outputting an enhancement-applied frame acoustic line signal to the B-mode image generator 4. The B-mode image generator 4 performs a brightness conversion by executing processing such as envelope detection, logarithmic compression, and so on on the acoustic line signal. A B-mode image signal is generated by applying a conversion into Cartesian coordinates to a resulting brightness signal. The B-mode image generator 4 outputs the resulting B-mode image signal to the display controller 7.

According to the above-described configuration, the acoustic line signal compounder 52A, the frame enhancement map compounder 65A, and the acoustic line signal enhancer 63A serve as an enhancement-applied acoustic line signal generator SA.

<Operations>

The operations of the ultrasound diagnostic device 10A, configured as described above, are described next. The operations are similar to the previously-described flowchart of FIG. 2, with the exception that the B-mode image signal is replaced by the acoustic line signal. FIG. 3 describes the operations of the ultrasound diagnostic device 10A.

As indicated in FIG. 3, as read from the top, performing sub-scans 1, 2, and 3 during ultrasound scan 1 results in sub-frame acoustic line signals 1, 2 and 3 being sequentially obtained in accordance with the acquired acoustic line signals. Then, a frame acoustic line signal (1+2+3) is generated by compounding these results.

Also, sub-frame enhancement maps are created in accordance with the sub-frame acoustic line signals, and a frame enhancement map (1+2+3) is generated by compounding the sub-frame enhancement maps. In this example, a sub-frame enhancement map is created each time a sub-scan is performed. However, the process may also occur at any desired time during ultrasound scan 1.

Enhancement is then applied to the frame acoustic line signal (1+2+3) in accordance with the frame enhancement map (1+2+3) to generate enhancement-applied frame acoustic line signal (1+2+3)×(k), which is output to the display controller 7.

Subsequently, as read in descending order in FIG. 3, ultrasound scans 2, 3, and 4 are performed. Each time, a frame acoustic line signal is created through compounding, a frame enhancement map is created through compounding, and an enhancement-applied frame acoustic line signal is generated. This group of processing is performed each time a new sub-scan is performed, by replacing an old sub-frame acoustic line signal with a newly-obtained sub-frame acoustic line signal. As such, the enhancement-applied frame acoustic line signal is output for each sub-scan, enabling smooth display.

(Conclusion)

The ultrasound diagnostic device 10A configured as described above produces the following effects, in addition to the effects of the ultrasound diagnostic device 10 pertaining to Embodiment 1.

The ultrasound diagnostic device 10A creates a sub-frame enhancement map for an acoustic line signal of a pixel region in accordance with a characteristic value calculated from the acoustic line signal of the pixel region. Accordingly, enhancement processing is performed on an acoustic line signal and not on a B-mode image signal, which enables determining the enhancement amount for the puncture needle based on the acoustic line signal and thus removing the influence of operator-specific picture adjustment reflected in the generation of a B-mode image. This enables the enhancement amount to be determined independently of the operator-specific adjustment. Also, the enhancement amount for the acoustic line signal of the pixel region is calculated in accordance with the characteristic value, which is the difference (amount of change) between the acoustic line signal for the pixel region and the acoustic line signal for a pixel region near the pixel region, in the sub-frame acoustic line signal. Accordingly, the sub-frame enhancement map is created without calculating the frame difference between sub-frame acoustic line signals. This enables the enhancement amount to be calculated independently of the operator-specific adjustment. Further, each time a sub-scan is performed, a new enhancement-applied frame acoustic line signal is output to the display controller 7, thus enabling smooth image display.

<Other Variations>

The ultrasound diagnostic device has been described above in terms of the Embodiments. However, the present disclosure is not particularly limited to the Embodiments, and is also modifiable as appropriate in accordance therewith.

Embodiment 1, as described above, involves step S204 of generating the enhancement-applied reception signal by performing sub-step S2041 of creating the frame enhancement map by averaging the sub-frame enhancement maps corresponding to a plurality of sub-frame reception signals, sub-step S2042 of generating a frame reception signal by compounding the sub-frame reception signals, and sub-step S2043 of applying enhancement to the frame reception signal by applying, to each pixel region reception signal included in the frame reception signal, an enhancement amount, included in the frame enhancement map, for a corresponding pixel region reception signal. However, step S204 of generating the enhancement-applied reception signal may be adjusted as appropriate, provided that the enhancement-applied reception signal is generated by compounding pixel region reception signals included in the sub-frame reception signals based on pixel region positions, while taking into account the enhancement amount included in at least one of the sub-frame enhancement maps. For example, step S204 of generating the enhancement-applied reception signal may include a sub-step of enhancement-applied sub-frame reception signals by applying, with respect to each pixel region reception signal included in each of the sub-frame reception signals, an enhancement amount, included in the corresponding sub-frame enhancement map, for a corresponding pixel region reception signal; and a sub-step of the enhancement-applied frame reception signal by averaging the enhancement-applied sub-frame reception signals. This results in similar results to those of the ultrasound diagnostic device 10 described above for Embodiment 1.

Also, in the above-described Embodiment, the B-mode image enhancer 63 applies the enhancement processing to the B-mode image signal so that a greater enhancement amount amplifies the brightness of a corresponding pixel region reception signal. However, no such limitation to the enhancement amount is intended. Appropriate adjustment may be made. For example, the B-mode image enhancer 63 may also apply the enhancement processing to the B-mode image signal so that a pixel region reception signal is displayed on the display apparatus in a different color, depending upon the enhancement amount. Also, the B-mode image enhancer 63 may apply the enhancement processing to the B-mode image signal such that a greater enhancement amount applied to a pixel region reception signal increases the amount of time for which the enhancement effect for the pixel region reception signal endures. This allows the enhancement effect to stand out when displayed.

Also, for example, in the above-described Embodiment, the ultrasound probe is an ultrasound probe in which a plurality of piezoelectric elements are arranged unidirectionally. However, the configuration of the ultrasound probe is not limited in this manner. For example, an ultrasound probe in which a plurality of piezoelectric transducers are arranged two-dimensionally may also be used. When such an ultrasound probe is used, the ultrasound beam that is transmitted may be controlled in terms of irradiation position and direction by individually altering the voltage and the timing of voltage application for the piezoelectric transducers.

Also, the ultrasound probe may include a functional portion of the ultrasound transmitter and receiver. For example, the ultrasound probe may internally generate an electronic transmission signal in accordance with a control signal output by the ultrasound transmitter and receiver for generating the electronic transmission signal, and convert the electronic transmission signal into the ultrasound. Correspondingly, the ultrasound probe may internally convert an electronic reception signal received as the reflected ultrasound and acquire the reception signal in accordance with the electric reception signal.

Also, the various processing of the ultrasound diagnostic device pertaining to the Embodiments may be realized by a large-scale integration (hereinafter, LSI), which is a typical integrated circuit. The components may be individually provided on single chips, or one or more components may be provided on a single chip.

Also, in the Embodiments, the blocks are described as independent hardware configurations. However, the blocks of the ultrasound diagnostic device need not necessarily be realized as independent hardware. For example, the various blocks may be combined as needed and the functions thereof may be realized by a central processing unit (CPU) and software.

Also, the functions of the functional blocks of the ultrasound diagnostic device may be realized in whole or in part by the LSI, which is a typical integrated circuit. The components may be individually provided on single chips, or one or more components may be provided on a single chip. Also, depending on the degree of integration, the LSI may be appropriately termed an integrated circuit (IC), a system LSI, a super LSI, or an ultra LSI.

Also, the integrated circuit method is not limited to LSI. A dedicated circuit or a general-purpose processor may also be used. After LSI manufacture, a Field Programmable Gate Array (FPGA) or re-configurable processor may also be used.

Furthermore, further advances in semiconductor technology and newly-appearing technology may replace LSI as integrated circuit technology, in which case such technology is, of course, usable for the integration of the functional blocks.

Also, the functions of the ultrasound diagnostic device pertaining to the Embodiments may, in whole or in part, be realized by a program executed by a processor in a CPU or similar.

Furthermore, the present disclosure may be a program as mentioned above, and the program may be recorded on a non-temporary computer-readable recording medium. Of course, the program may be distributed through a delivery medium such as the Internet.

Also, the division of functional blocks in the block diagrams is merely an example. A plurality of functional blocks may be regrouped into one functional block, one functional block may be subdivided into a plurality of functional blocks, and the functions of one functional block may be transferred to another functional block. In addition, a plurality of functional blocks having similar functions may be realized by parallel processing or time-division processing on common hardware or software.

Also, the execution order of the steps described above is merely an example given for explanatory purposes. Other ordering is also applicable. Also, the above-described steps may be partially performed simultaneously (in parallel).

Furthermore, the ultrasound diagnostic device pertaining to the Embodiments and the Variations thereof may be at least partially combined.

In addition, further variations on the present disclosure within the scope of consideration for those skilled in the art are included within the scope of the disclosure.

<Summary>

As described above, an ultrasound image processing method pertaining to the Embodiments generates a frame reception signal by compounding a plurality of sub-frame reception signals acquired from a subject body through an ultrasound probe. The sub-frame reception signals are each generated through one of a plurality of sub-scans composing an ultrasound scan, and between the sub-scans, a range in the subject body that is scanned differs due to a different one of a plurality of ultrasound beam steering angles being used. The ultrasound image processing method includes: acquiring the sub-frame reception signals (S201); creating a plurality of sub-frame enhancement maps, each corresponding to one of the sub-frame reception signals, the creating of each of the sub-frame enhancement maps being performed by calculating, for a pixel region reception signal included in a corresponding one of the sub-frame reception signals, an enhancement amount in accordance with a characteristic value calculated based on the pixel region reception signal, the pixel region reception signal corresponding to a pixel region composed of one or more pixels (S202); and generating an enhancement-applied frame reception signal by compounding pixel region reception signals included in the sub-frame reception signals based on pixel region positions, while taking into account the enhancement amount included in at least one of the sub-frame enhancement maps (S204).

An ultrasound diagnostic device pertaining to the Embodiments generates a frame reception signal by compounding a plurality of sub-frame reception signals acquired from a subject body through an ultrasound probe. The sub-frame reception signals are each generated through one of a plurality of sub-scans composing an ultrasound scan, and between the sub-scans, a range in the subject body that is scanned differs due to a different one of a plurality of ultrasound beam steering angles being used. The ultrasound diagnostic device includes a control circuit. The control circuit includes: a reception signal acquirer (51) acquiring the sub-frame reception signals; a sub-frame enhancement map creator (62) creating a plurality of sub-frame enhancement maps, each corresponding to one of the sub-frame reception signals, the creating of each of the sub-frame enhancement maps being performed by calculating, for a pixel region reception signal included in a corresponding one of the sub-frame reception signals, an enhancement amount in accordance with a characteristic value calculated based on the pixel region reception signal, the pixel region reception signal corresponding to a pixel region composed of one or more pixels; and an enhancement-applied reception signal generator (S) generating an enhancement-applied frame reception signal by compounding pixel region reception signals included in the sub-frame reception signals based on pixel region positions, while taking into account the enhancement amount included in at least one of the sub-frame enhancement maps.

Also, in another aspect, the enhancement-applied reception signal generator (S) includes: a frame enhancement map compounder (65) creating a frame enhancement map by compounding the sub-frame enhancement maps, in accordance with a correction condition pertaining to the ultrasound beam steering angles respectively used to acquire the sub-frame reception signals; a reception signal compounder (52) generating a frame reception signal by compounding the sub-frame reception signals; and a reception signal enhancer (63) applying enhancement to the frame reception signal by applying, with respect to each pixel region reception signal included in the frame reception signal, an enhancement amount, included in the frame enhancement map, for a corresponding pixel region reception signal.

According to the ultrasound image processing method of the present disclosure and the ultrasound diagnostic device using the method, the above-described configuration enables a frame enhancement map to be created by mapping an appropriate enhancement amount to a puncture needle, thus increasing visibility of the puncture needle in an ultrasound image diagnostic using spatial compounding. Thus, improvements to ultrasound diagnostic device usability are provided to the operator. Accordingly, the ultrasound image processing method and the ultrasound diagnostic device using the method are widely applicable.

<Supplement>

The above-described Embodiments each describe a specific beneficial example of the disclosure. The numerical values, shapes, materials, components, component positions and connectivity, steps, ordering of steps, and so on mentioned in the Embodiments are examples and are not intended to limit the disclosure. Also, any steps not described in an independent aspect representing a top-level concept of the disclosure are described as optional beneficial components, among the components of the Embodiments.

Also, for ease of understanding, the component dimensions in the drawings illustrating the Embodiments may differ from reality. No limitation to the disclosure is intended by the Embodiments. Appropriate variations are applicable provided that these do not exceed the scope of the disclosure.

Furthermore, lead lines are present as materials on the circuit components provided on a substrate in the ultrasound diagnostic device. However, various arrangements of such electronic lines and electronic circuits are possible in accordance with common technical knowledge in the relevant fields. Explanations thereof are thus omitted given the lack of direct relevance to the disclosure. Also, the various drawings are schematics and may not closely represent reality.

Although the present disclosure has been fully described by way of examples with reference to the accompanying drawings, it is to be noted that various changes and modifications will be apparent to those skilled in the art. Therefore, unless such changes and modifications depart from the scope of the present disclosure, they should be construed as being included therein.

What is claimed is:

1. An ultrasound diagnostic device generating a frame reception signal by compounding a plurality of sub-frame reception signals acquired from a subject body through an ultrasound probe, wherein the sub-frame reception signals are each generated through one of a plurality of sub-scans composing an ultrasound scan, and between the sub-scans, a range in the subject body that is scanned differs due to a different one of a plurality of ultrasound beam steering angles being used, the ultrasound diagnostic device comprising a control circuit, the control circuit including:

a reception signal acquirer that acquires the sub-frame reception signals;

a sub-frame enhancement map creator that creates a plurality of sub-frame enhancement maps, each corresponding to one of the sub-frame reception signals, the creating of each of the sub-frame enhancement maps being performed by calculating, for a pixel region reception signal included in a corresponding one of the sub-frame reception signals, a sub-frame reception signal enhancement amount in accordance with a characteristic value calculated based on the pixel region reception signal, the pixel region reception signal corresponding to a pixel region composed of one or more pixels; and an enhancement-applied reception signal generator that generates an enhancement-applied frame reception signal by compounding pixel region reception signals included in the sub-frame reception signals based on pixel region positions, and applying an enhancement based on the sub-frame reception signal enhancement amount included in at least one of the sub-frame enhancement maps, whereby the enhancement-applied frame reception signal is a signal to which the enhancement has been applied based on the sub-frame reception signal enhancement amount included in said at least one of the sub-frame enhancement maps, wherein the enhancement-applied reception signal generator includes:

a reception signal generator that generates a frame reception signal by compounding the sub-frame reception signals; and a reception signal enhancer that applies the enhancement to the frame reception signal by applying, with respect to each pixel region reception signal included in the frame reception signal, a frame reception signal enhancement amount for a corresponding pixel region reception signal, the frame reception signal enhancement amount being determined based on the sub-frame reception signal enhancement amount included in said at least one of the sub-frame enhancement maps, wherein the enhancement-applied reception signal generator increases the frame reception signal enhancement amount for the corresponding pixel region reception signal to be asymptotic to an upper limit value such that, in a case in which the frame reception signal enhancement amount for the corresponding pixel region reception signal is not less than a predetermined threshold, the frame reception signal is increased to and capped at the upper limit value.

2. The ultrasound diagnostic device of claim 1,
wherein the enhancement-applied reception signal generator further includes a frame enhancement map compounder that creates a frame enhancement map by averaging the sub-frame enhancement maps of the sub-frame reception signals; and
wherein the reception signal enhancer applies the enhancement to the frame reception signal by applying, with respect to each pixel region reception signal included in the frame reception signal, the frame reception signal enhancement amount for the corresponding pixel region reception signal, the frame reception signal enhancement amount being included in the frame enhancement map.

3. The ultrasound diagnostic device of claim 1,
wherein the enhancement-applied reception signal generator further includes
a frame enhancement map compounder creating a frame enhancement map by compounding the sub-frame enhancement maps, in accordance with a correction condition pertaining to the ultrasound beam steering angles respectively used to acquire the sub-frame reception signals; and
wherein the reception signal enhancer applies the enhancement to the frame reception signal by applying, with respect to each pixel region reception signal included in the frame reception signal, the frame reception signal enhancement amount for the corresponding pixel region reception signal, the frame reception signal enhancement amount being included in the frame enhancement map.

4. The ultrasound diagnostic device according to claim 1, wherein the control circuit further includes a display controller that controls a display to display an image generated based on the enhancement-applied frame reception signal.

* * * * *